(12) United States Patent
Bonnette et al.

(10) Patent No.: US 11,497,522 B2
(45) Date of Patent: Nov. 15, 2022

(54) INFUSION LUBRICATED ATHERECTOMY CATHETER

(71) Applicant: BOSTON SCIENTIFIC LIMITED, Hamilton (BM)

(72) Inventors: Michael J. Bonnette, Minneapolis, MN (US); Richard R. Prather, St. Michael, MN (US); Debra M. Kozak, Forest Lake, MN (US); David B. Morris, Anoka, MN (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 459 days.

(21) Appl. No.: 16/785,865

(22) Filed: Feb. 10, 2020

(65) Prior Publication Data

US 2020/0170663 A1 Jun. 4, 2020

Related U.S. Application Data

(63) Continuation of application No. 15/822,384, filed on Nov. 27, 2017, now Pat. No. 10,595,893, which is a
(Continued)

(51) Int. Cl.
*A61B 17/3207* (2006.01)
*A61M 25/00* (2006.01)
(Continued)

(52) U.S. Cl.
CPC .. *A61B 17/3207* (2013.01); *A61B 17/320758* (2013.01); *A61M 1/0058* (2013.01);
(Continued)

(58) Field of Classification Search
CPC ............... A61B 17/32; A61B 17/3207; A61B 17/320758; A61M 1/85; A61M 1/0058; A61M 2025/0031
See application file for complete search history.

(56) References Cited

U.S. PATENT DOCUMENTS 4,998,527 A 3/1991 Meyer et al.
5,152,744 A 10/1992 Krause et al.
(Continued)

FOREIGN PATENT DOCUMENTS

WO 01/76680 A1 10/2001
WO 2009065078 A1 5/2009
WO 2014008599 A1 1/2014

*Primary Examiner* — Deanna K Hall
(74) *Attorney, Agent, or Firm* — Seager, Tufte & Wickhem LLP

(57) ABSTRACT

A matter elimination catheter includes a catheter body extending from a catheter proximal portion to a catheter distal portion. The catheter body includes an infusion lumen, an aspiration lumen fluidly isolated from the infusion lumen, and a septum interposed between the infusion and aspiration lumens. A drive shaft is within the infusion lumen and is configured to provide rotation near the catheter distal portion. A guide wire lumen is within the drive shaft, and the infusion lumen, the drive shaft and the guide wire lumen are fluidly separated from the aspiration lumen with the septum. In one example, fluid bearings are formed between one or more of the catheter body and drive shaft or the drive shaft and a guide wire or guide wire liner when supplied with infusion fluid through the infusion lumen.

20 Claims, 17 Drawing Sheets

Related U.S. Application Data continuation of application No. 14/640,110, filed on Mar. 6, 2015, now Pat. No. 9,855,070.

(60) Provisional application No. 61/951,856, filed on Mar. 12, 2014.

(51) Int. Cl.
*A61M 1/00* (2006.01)
*A61M 25/06* (2006.01)

(52) U.S. Cl.
CPC ............ *A61M 1/85* (2021.05); *A61M 25/003* (2013.01); *A61M 25/0023* (2013.01); *A61B 2017/320716* (2013.01); *A61B 2017/320775* (2013.01); *A61M 25/0662* (2013.01); *A61M 25/0668* (2013.01); *A61M 2025/0024* (2013.01); *A61M 2025/0031* (2013.01)

(56) References Cited

U.S. PATENT DOCUMENTS

| | | |
|---|---|---|
| 5,181,911 A | 1/1993 | Shturman et al. |
| 5,190,046 A | 3/1993 | Shturman |
| 5,221,258 A | 6/1993 | Shturman |
| 5,295,958 A | 3/1994 | Shturman |
| 5,312,427 A | 5/1994 | Shturman |
| 5,314,438 A | 5/1994 | Shturman et al. |
| 5,331,947 A | 7/1994 | Shturman |
| 5,356,418 A | 10/1994 | Shturman |
| 5,360,432 A | 11/1994 | Shturman et al. |
| 5,443,446 A | 8/1995 | Shturman |
| 5,554,163 A | 9/1996 | Shturman |
| 5,779,722 A | 7/1998 | Shturman et al. |
| 5,843,103 A | 12/1998 | Wulfman |
| 5,893,857 A | 4/1999 | Shturman et al. |
| 5,897,566 A | 4/1999 | Shturman et al. |
| 5,916,227 A | 6/1999 | Keith et al. |
| 6,024,749 A | 2/2000 | Shturman et al. |
| 6,027,460 A | 2/2000 | Shturman |
| 6,039,747 A | 3/2000 | Shturman et al. |
| 6,077,282 A | 6/2000 | Shturman et al. |
| RE36,764 E | 7/2000 | Zacca et al. |
| 6,129,734 A | 10/2000 | Shturman et al. |
| 6,132,444 A | 10/2000 | Shturman et al. |
| 6,217,595 B1 | 4/2001 | Shturman et al. |
| 6,295,712 B1 | 10/2001 | Shturman et al. |
| 6,494,890 B1 | 12/2002 | Shturman et al. |
| 6,565,588 B1 | 5/2003 | Clement et al. |
| 6,579,298 B1 | 6/2003 | Bruneau et al. |
| 6,638,288 B1 | 10/2003 | Shturman et al. |
| 6,808,508 B1 | 10/2004 | Zafirelis et al. |
| 6,818,001 B2 | 11/2004 | Wulfman et al. |
| 6,824,550 B1 | 11/2004 | Noriega et al. |
| 6,852,118 B2 | 2/2005 | Shturman et al. |
| 7,174,240 B2 | 2/2007 | Shturman et al. |
| 7,344,546 B2 | 3/2008 | Wulfman et al. |
| 7,485,127 B2 | 2/2009 | Nistal |
| 7,507,245 B2 | 3/2009 | Shturman et al. |
| D600,792 S | 9/2009 | Eubanks et al. |
| 7,584,022 B2 | 9/2009 | Shturman et al. |
| 7,666,202 B2 | 2/2010 | Prudnikov et al. |
| 7,674,272 B2 | 3/2010 | Torrance et al. |
| 7,713,231 B2 | 5/2010 | Wulfman et al. |
| 7,713,235 B2 | 5/2010 | Torrance et al. |
| 7,842,009 B2 | 11/2010 | Torrance et al. |
| 8,162,964 B2 | 4/2012 | Piippo et al. |
| 8,177,801 B2 | 5/2012 | Kallok et al. |
| 8,192,451 B2 | 6/2012 | Cambronne et al. |
| 8,348,965 B2 | 1/2013 | Prudnikov et al. |
| 8,353,923 B2 | 1/2013 | Shturman |
| 8,439,937 B2 | 5/2013 | Montague et al. |
| 8,475,478 B2 | 7/2013 | Robinson |
| 8,551,128 B2 | 10/2013 | Hanson et al. |
| 8,551,130 B2 | 10/2013 | Schoenle et al. |
| 8,568,354 B2 | 10/2013 | Schoenle et al. |
| 8,597,313 B2 | 12/2013 | Thatcher et al. |
| 8,628,550 B2 | 1/2014 | Narveson |
| 8,628,551 B2 | 1/2014 | Hanson et al. |
| 8,632,557 B2 | 1/2014 | Thatcher et al. |
| 8,702,735 B2 | 4/2014 | Rivers |
| 8,758,377 B2 | 6/2014 | Rivers et al. |
| 8,795,303 B2 | 8/2014 | McBroom et al. |
| 8,795,304 B2 | 8/2014 | Piippo Svendsen et al. |
| 8,974,519 B2 | 3/2015 | Gennrich et al. |
| 2002/0029056 A1 | 3/2002 | Hall et al. |
| 2002/0169467 A1 | 11/2002 | Heitzmann et al. |
| 2003/0139689 A1 | 7/2003 | Shturman et al. |
| 2003/0199889 A1 | 10/2003 | Kanz et al. |
| 2004/0006358 A1 | 1/2004 | Wulfman et al. |
| 2004/0181249 A1 | 9/2004 | Torrance et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0243162 A1 | 12/2004 | Wulfman et al. |
| 2005/0149083 A1 | 7/2005 | Prudnikov et al. |
| 2006/0249205 A1 | 11/2006 | Shturman et al. |
| 2006/0258976 A1 | 11/2006 | Shturman et al. |
| 2006/0271242 A1 | 11/2006 | Shturman et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0228208 A1 | 9/2008 | Wulfman et al. |
| 2009/0018564 A1 | 1/2009 | Shturman |
| 2009/0069829 A1 | 3/2009 | Shturman |
| 2009/0182359 A1 | 7/2009 | Shturman |
| 2009/0306689 A1 | 12/2009 | Welty et al. |
| 2009/0306690 A1 | 12/2009 | Rivers et al. |
| 2010/0100110 A1 | 4/2010 | Cambronne et al. |
| 2010/0121361 A1 | 5/2010 | Plowe et al. |
| 2010/0174302 A1 | 7/2010 | Heitzmann et al. |
| 2010/0324472 A1 | 12/2010 | Wulfman |
| 2011/0009888 A1 | 1/2011 | Shturman |
| 2011/0040238 A1 | 2/2011 | Wulfman et al. |
| 2011/0071440 A1 | 3/2011 | Torrance et al. |
| 2011/0077673 A1 | 3/2011 | Grubac et al. |
| 2011/0087254 A1 | 4/2011 | Welty |
| 2011/0106004 A1 | 5/2011 | Eubanks et al. |
| 2011/0112562 A1 | 5/2011 | Torrance |
| 2011/0118660 A1 | 5/2011 | Torrance et al. |
| 2011/0151463 A1 | 6/2011 | Wulfman |
| 2011/0213391 A1 | 9/2011 | Rivers et al. |
| 2011/0300010 A1 | 12/2011 | Jarnagin et al. |
| 2012/0041307 A1 | 2/2012 | Patel et al. |
| 2012/0041359 A1 | 2/2012 | Schoenle et al. |
| 2012/0046599 A1 | 2/2012 | Schoenle et al. |
| 2012/0046600 A1 | 2/2012 | Kohler et al. |
| 2012/0109105 A1 | 5/2012 | Cambronne |
| 2012/0109171 A1 | 5/2012 | Zeroni et al. |
| 2012/0116431 A1 | 5/2012 | Shturman et al. |
| 2012/0191121 A1 | 7/2012 | Chen et al. |
| 2013/0018398 A1 | 1/2013 | Rivers et al. |
| 2013/0018399 A1 | 1/2013 | Rivers et al. |
| 2013/0023913 A1 | 1/2013 | Rivers et al. |
| 2013/0253552 A1 | 9/2013 | Schoenle et al. |
| 2014/0005699 A1 | 1/2014 | Bonnette et al. |
| 2014/0081298 A1 | 3/2014 | Cambronne |
| 2014/0277014 A1 | 9/2014 | Higgins et al. |
| 2014/0316447 A1 | 10/2014 | Ellering et al. |
| 2014/0316448 A1 | 10/2014 | Higgins |
| 2014/0316449 A1 | 10/2014 | Grothe et al. |
| 2014/0316450 A1 | 10/2014 | Higgins |
| 2014/0316451 A1 | 10/2014 | Higgins et al. |
| 2014/0350582 A1 | 11/2014 | Higgins |
| 2014/0364883 A1 | 12/2014 | Schoenle et al. |
| 2014/0365691 A1 | 12/2014 | Schoenle et al. |
| 2014/0371770 A1 | 12/2014 | Schoenle et al. |
| 2015/0005791 A1 | 1/2015 | Schoenle et al. |
| 2015/0051626 A1 | 2/2015 | Rivers et al. |
| 2015/0073447 A1 | 3/2015 | Rydberg et al. |
| 2015/0073448 A1 | 3/2015 | Rydberg |
| 2015/0080747 A1 | 3/2015 | Schoenle |

(56) References Cited

U.S. PATENT DOCUMENTS

| | | |
|---|---|---|
| 2015/0080795 A1 | 3/2015 | Mattison et al. |
| 2015/0089785 A1 | 4/2015 | Blackledge et al. |
| 2015/0094745 A1 | 4/2015 | Blackledge et al. |
| 2015/0094749 A1 | 4/2015 | Ellering et al. |
| 2015/0112371 A1 | 4/2015 | Rydberg et al. |
| 2015/0119909 A1 | 4/2015 | Rydberg |
| 2015/0127033 A1 | 5/2015 | Rydberg et al. |
| 2015/0133974 A1 | 5/2015 | Karasti et al. |
| 2015/0133975 A1 | 5/2015 | Rydberg et al. |
| 2015/0133976 A1 | 5/2015 | Johnson et al. |

INFUSION LUBRICATED ATHERECTOMY CATHETER

CROSS-REFERENCE TO RELATED APPLICATIONS

This application is a continuation of U.S. patent application Ser. No. 15/822,384, filed Nov. 27, 2017, which is a continuation of U.S. patent application Ser. No. 14/640,110, filed Mar. 6, 2015, now U.S. Pat. No. 9,855,070, which claims priority to U.S. Provisional Application No. 61/951,856, filed Mar. 12, 2014, the entire disclosures of which are incorporated herein by reference.

TECHNICAL FIELD

This document pertains generally, but not by way of limitation, to atherectomy and thrombectomy systems and catheters.

BACKGROUND

Atherectomy and thrombectomy are procedures for removing plaques and thrombus from the vasculature. Plaques are more robust and anchored to the vessel walls relative to thrombus, which has a softer consistency and is more easily removed from the vessel.

In some examples, atherectomy catheters remove plaques from vessel walls through mechanical engagement and abrasion of plaques. The mechanical removal of plaques generates loose particulate matter within the vessel wall that increases the risk of emboli within the blood stream.

Similarly, in some examples, thrombectomy procedures remove thrombus from vessel walls through mechanical systems that mechanically engage and remove thrombus, for instance by cutting of the thrombus with one or more features at the end of a catheter. In still other examples, catheters include hydrodynamic features that generate streams of solution, such as saline, that engage with thrombus and hydrodynamically remove thrombus from the vessel walls. In yet other examples, solutions such as lytic medicants are delivered to thrombus within the vasculature, and the medicants breakdown the thrombus.

In some examples, atherectomy catheters include cutters coupled with a drive shaft to mechanically abrade plaques. The drive shaft extends through an aspiration lumen. Effluent (infusion fluid including entrained particulate) flows around the drive shaft during use of the catheter including rotation of the drive shaft to accordingly rotate the cutters. In still other examples, guide wires are delivered through the drive shaft to a distal portion of the catheter and into the vasculature. The catheter is translated through the vasculature according to the track of the guide wire. Because the drive shaft is within the aspiration lumen the guide wire is also positioned within the aspiration lumen with the effluent during operation.

Infusion fluid is delivered through an infusion lumen extending through the catheter body. The aspiration lumen also extends through the catheter body and is adjacent to the infusion lumen. The infusion fluid is delivered through the infusion lumen at an elevated pressure, for instance from 50 to 500 psi. The elevated pressure ensures the infusion fluid is delivered under pressure to the catheter distal portion for entrainment of particulate for eventual aspiration through the aspiration lumen and/or to provide for balanced inflows and outflows, as well as lubrication of moving components.

BRIEF SUMMARY

The disclosure is directed to several alternative designs, materials and methods of manufacturing medical device structures and assemblies, and uses thereof.

In one example, a matter elimination catheter is disclosed. The catheter includes a catheter body extending from a catheter proximal portion to a catheter distal portion. The catheter body includes an infusion lumen, an aspiration lumen fluidly isolated from the infusion lumen, and a septum of the catheter body interposed between the infusion and aspiration lumens. The catheter also includes a drive shaft within the infusion lumen and a guide wire lumen within the drive shaft. The drive shaft is configured to provide rotation near the catheter distal portion. The infusion lumen, the drive shaft and the guide wire lumen are fluidly separated from the aspiration lumen with the septum.

Additionally or alternatively, in another example, the septum spans the catheter body from a first portion of a catheter body side wall to a second portion of the catheter body side wall.

Additionally or alternatively, in another example, the catheter includes an outflow port near the catheter distal portion in communication with the infusion lumen near the catheter distal portion and an inflow port near the catheter distal portion in communication with the aspiration lumen near the catheter distal portion.

Additionally or alternatively, in another example, the catheter includes an infusion fluid source in communication with the infusion lumen and configured to provide a source of pressurized infusion fluid through the infusion lumen and the outflow port; and an aspiration source in communication with the aspiration lumen and configured to aspirate the infusion fluid with entrained matter and/or with blood as an aspirant dilutant through the inflow port and the aspiration lumen. In an operational mode the infusion fluid entrains matter from a vessel between the at least one outflow port and the inflow port, and the entrained matter and infusion fluid are delivered to the catheter proximal portion through the aspiration lumen. The infusion fluid may also maintain an isovolumetric treatment site so the vessel does not have a tendency to suck down or collapse with vacuum pressure, as well as provide lubrication to lubricate the cutter and the drive shaft, bearings, and other moving components.

Additionally or alternatively, in another example, in a pressurized configuration pressure of the infusion fluid within the infusion lumen is greater than pressure of the infusion fluid with entrained matter exterior of the aspiration lumen, and the infusion fluid with entrained matter is directed away from the drive shaft within the infusion lumen according to the pressure difference.

Additionally or alternatively, in another example, the catheter includes a guide wire liner within the guide wire lumen of the drive shaft, wherein the drive shaft is rotatable relative to the guide wire liner.

Additionally or alternatively, in another example, the catheter includes one or more fluid bearings isolated from the aspiration lumen and generated with pressurized infusion fluid delivered through the infusion lumen.

Additionally or alternatively, in another example, the one or more fluid bearings include one or more of fluid dynamic bearings or hydrostatic bearings.

Additionally or alternatively, in another example, the catheter includes at least one shaft fluid bearing interposed between the catheter body and the drive shaft in the infusion lumen, and the at least one shaft fluid bearing is generated with pressurized infusion fluid delivered through the infusion lumen.

Additionally or alternatively, in another example, the at least one shaft fluid bearing extends from the catheter proximal portion to the catheter distal portion.

Additionally or alternatively, in another example, the at least one shaft fluid bearing extends the length of the drive shaft.

Additionally or alternatively, in another example, the catheter includes at least one guide wire fluid bearing interposed between the drive shaft and at least one of a guide wire or a guide wire liner in the guide wire lumen, wherein the at least one guide wire fluid bearing is generated with pressurized infusion fluid delivered through the infusion lumen and penetrating the drive shaft.

Additionally or alternatively, in another example, the drive shaft is coupled to at least one rotatable cutter near the catheter distal portion, and the drive shaft and the at least one rotatable cutter are rotatable relative to the catheter body.

Additionally or alternatively, in another example, the catheter includes at least one cutter fluid bearing interposed between the rotatable cutter and the catheter body, wherein the at least one cutter fluid bearing is formed between a cutter interface and a catheter body interface with pressurized infusion fluid delivered from the infusion lumen.

Another example is a matter elimination catheter including a catheter body extending from a catheter proximal portion to a catheter distal portion. The catheter body includes an infusion lumen in fluid communication with at least one outflow port near the catheter distal portion, an aspiration lumen isolated from the infusion lumen, and a septum of the catheter body interposed between the infusion and aspiration lumens. The catheter also includes a drive shaft within the infusion lumen. The drive shaft is configured to provide rotation near the catheter distal portion. In an infusion configuration, an infusion fluid is delivered through the infusion lumen to the at least one outflow port and/or along the bearings, cutters, drive shaft or other rotatable catheter components in juxtaposition with static components. The drive shaft and a portion of the catheter body associated with the infusion lumen are configured to provide at least one shaft fluid bearing therebetween with the infusion fluid. The at least one outflow port is configured to provide a fluid barrier with the infusion fluid to prevent ingress of infusion fluid with entrained matter into the infusion lumen.

Additionally or alternatively, in another example, the catheter includes a manifold coupled to the catheter proximal portion. The manifold includes an infusion port configured to deliver infusion fluid to the infusion lumen and a diversion sleeve extending proximally relative to the infusion port, the drive shaft rotatably extending through the diversion sleeve.

Additionally or alternatively, in another example, in the infusion configuration the infusion fluid is directed distally over an exterior perimeter of the diversion sleeve, and at a distal end of the diversion sleeve a first portion of the infusion fluid flows distally through the infusion lumen toward the catheter distal portion and a second portion of the infusion fluid flows proximally along an interior perimeter of the diversion sleeve. The first and second portions are controlled by the dimensions between an inner diameter of the diversion sleeve and an outer diameter of the drive shaft.

Additionally or alternatively, in another example, the second portion of the infusion fluid forms a shaft fluid bearing between the diversion sleeve and the drive shaft.

Additionally or alternatively, in another example, the catheter includes a guide wire extending through the drive shaft, wherein the first portion of the infusion fluid forms a guide wire fluid bearing between the drive shaft and the guide wire extending through the drive shaft.

Additionally or alternatively, in another example, the catheter includes a guide wire liner extending through the drive shaft, wherein the first portion of the infusion fluid forms a guide wire fluid bearing between the drive shaft and the guide wire liner extending through the drive shaft..

The above summary of some example embodiments is not intended to describe each disclosed embodiment or every implementation of the aspects of the disclosure.

BRIEF DESCRIPTION OF THE DRAWINGS

The aspects of the disclosure may be further understood in consideration of the following detailed description of various embodiments in connection with the accompanying drawings, in which.

Figure 1:
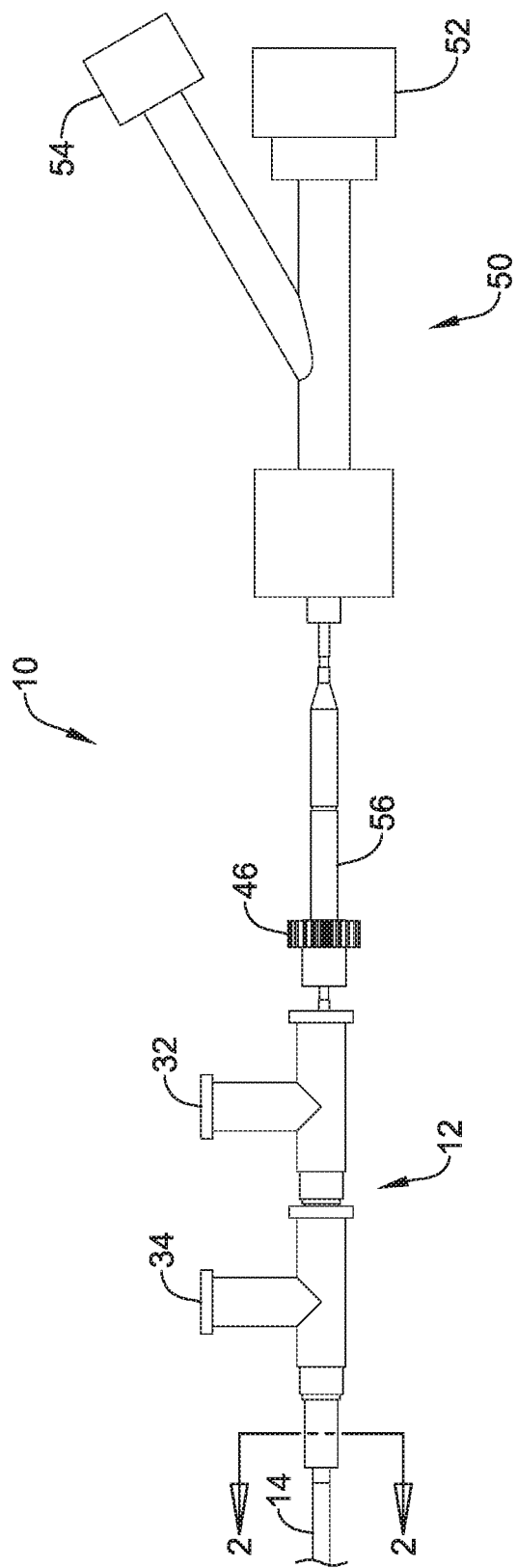
FIG. 1 is a side plan view of a proximal end region of an exemplary matter elimination catheter in accordance with this disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. Accordingly, the terms "a" or "an" are used, as is common in patent documents, to include one or more than one, independent of any other instances or usages of "at least one" or "one or more". As used in this specification and the appended claims, the term "or" is generally employed to include "and/or," unless the content clearly dictates otherwise. Accordingly, the term "or" is used to refer to a nonexclusive or, such that "A or B" includes "A but not B," "B but not A," and "A and B," unless otherwise indicated. As used in this specification and the appending claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the event of inconsistent usages between this document and any documents so incorporated by reference, the usage in this document controls.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The present inventors have recognized, among other things, that a problem to be solved can include the fouling of the aspiration lumen with particulate matter including fibrin, plaques and thrombus. Fouling is particularly problematic with a drive shaft in the aspiration lumen as rotation of the drive shaft may be prevented. Still further, fouling may not prevent rotation of the drive shaft, but it may cause seizing of a guide wire by the drive shaft with the guide wire positioned in vasculature. Rotation of the seized guide wire within vasculature should be avoided.

In an example, the present subject matter can provide a solution to these and other problems, such as by isolating the drive shaft and a guide wire or guide wire liner within the drive shaft from the effluent within the aspiration lumen. In one example, the drive shaft and the guide wire lumen interior to the drive shaft extend through an infusion lumen that is isolated from the aspiration lumen where the effluent is directed during operation of a catheter. A septum between the aspiration and infusion lumens isolates the drive shaft. Infusion fluid delivered along the infusion lumen is clean (e.g., without particulate, such as fibrin, that may cause seizing of the drive shaft) and lubricates the drive shaft to facilitate rotation without the risk of fouling. Suitable infusion fluids include, but are not limited to, saline. Other suitable infusion fluids which are lubricants made for rotational atherectomy devices include Rotaglide® and Viperslide®. In certain embodiments, the infusion includes a medicament, such as, but not limited to, anti-restenosis or anti-thrombosis medicaments. Similarly, by isolating the guide wire and a guide wire lumen from the effluent the seizing of the guide wire by the drive shaft is substantially prevented. Further, the clean infusion fluid provides a lubricant to facilitate the movement of the catheter relative to the guide wire.

Further still, the infusion fluid is delivered at an elevated pressure, for instance 50 to 500 psi (100 to 250 psi or 50 to 100 psi). The pressurized and clean infusion fluid is delivered along the length of the drive shaft within the infusion lumen. The infusion fluid is eventually delivered through one or more outflow ports near a catheter distal portion. In one example, the outflow ports are dedicated ports that provide a cyclical flow of fluid configured to entrain loose particulate for eventual delivery to an inflow port of the aspiration lumen. In another example, the outflow ports include virtual ports provided between rotating features of the catheter, such as the interfaces of the catheter body (e.g., between one or more of catheter body material, saddle or a fitting) and the rotatable cutters. As described herein the infusion fluid provides a fluid barrier at these outflow ports. The outflow of infusion fluid from the outflow ports generates a fluid barrier that substantially prevents the ingress of particulate (e.g., thrombus or plaques) into the infusion lumen. In one example, the fluid barriers are generated by a pressure differential between the infusion fluid in the infusion lumen and the effluent outside of the infusion lumen. Accordingly, in another example, the drive shaft and a guide wire therein are substantially protected from fouling through a combination of the isolation of the infusion lumen from the aspiration lumen and the fluid barrier at each of the outflow ports. Furthermore, in some instances the cutting action may be enhanced by the action of displacing particles and reducing heat friction with the infusion fluid.

The present inventors have further recognized, among other things, that a problem to be solved can include minimization of rotational friction between a rotating drive shaft of a catheter and one or more of the catheter body and a guide wire. As described above, translational and rotational friction, including seizing of a guide wire is a negative outcome. Accordingly, minimizing translational and rotational friction for both the drive shaft and the guide wire caused by one or more of mechanical engagement of features (e.g., drive shaft to guide wire or catheter body) or effluent including particulate is desired.

In an example, the present subject matter can provide a solution to this problem, such as by isolating the drive shaft and a guide wire or guide wire liner within the drive shaft from the effluent and providing a flow of clean infusion fluid that may also act as a lubricant. As described herein, the drive shaft and guide wire lumen within the drive shaft are isolated from an aspiration lumen by placement within an infusion lumen. The pressurized flow of "clean" infusion fluid along the length of the drive shaft and the guide wire lubricates both the drive shaft and the guide wire and facilitates translation and/or rotation of both (e.g., relative to each other and the catheter body).

In addition to the provision of a clean lubricant, the drive shaft and the guide wire (or guide wire lumen liner) are both subject to pressurized infusion fluid that forms at least one fluid bearing (e.g., fluid dynamic bearings or hydrostatic bearings) extending between and optionally including moving portions of the catheter distal end, such as a rotating cutter (e.g., a one or more of a first cutter and a second cutter); or locations where prevention of ingress of effluent is desired. For instance, a fluid bearing of the drive shaft extends from the catheter proximal portion to the termination of the drive shaft near the catheter distal portion. The infusion fluid is positioned between the drive shaft and the catheter body, and penetrates the drive shaft under pressure to provide a fluid bearing between the drive shaft interior and a guide wire and/or guide wire liner. The resulting at least one fluid bearing facilitates rotation and/or translation of the drive shaft and the guide wire even in the most tortuous of vasculature. Further, the at least one fluid bearing facilitates the easy translation of the catheter over the guide wire or the converse. Additionally, at least one fluid bearing prevents the transmission of rotation from the drive shaft to the guide wire and thereby minimizes rotation of the guide wire within vasculature. The fluid bearings reduce the need for precise machining and maintenance of mechanical bearings needed with rotational features, such as cutters, in other designs.

Moreover, as described above, the high pressure infusion fluid used to infuse and lubricate is delivered to one or more rotatable cutters near the catheter distal portion. The infusion fluid is directed between interfaces of the cutters and the catheter body (e.g., catheter body material, fittings, or the like). The infusion fluid provides a lubricant layer and fluid bearing at these interfaces to facilitate the rotation of the cutters and substantially prevent the transmission of rotation or seizing of the cutters by engagement with the catheter tube, sleeves, or the like with the cutters.

The lubrication of the interfaces between the drive shaft, the catheter body and one or more of a guide wire or guide wire liner facilitates a minimized construction for the proximal manifold of the system including the infusion and aspiration ports and the motor coupled with the drive shaft. For instance, multiple speed configurations and controls for the same can be removed as seizing of the drive shaft on the guide wire is eliminated (minimized or eliminated) in favor of reliable operation of the drive shaft to rotate the cutters at a desired speed. Additionally, anchoring features including, but not limited to, clamps, septums and the like used to grasp a guide wire and prevent movement, such as rotation, of the guide wire are obviated with the isolation of the drive shaft and the guide wire in the infusion lumen and the provision of one or more fluid bearings as provided herein. In one example, the manifold of the system includes the infusion and aspiration ports coupled with the corresponding infusion fluid and aspiration sources, a motor coupled with the drive shaft (e.g., by a pinion gear), and an optional Tuohy-Borst adapter for the introduction of the guide wire to the infusion lumen and the guide wire lumen of the drive shaft.

The optional Tuohy-Borst adapter assists in priming the guide wire lumen (e.g., within the drive shaft) in a construction using the guide wire liner (described herein). The need for rotational guide wire exchange (REX), an exchange technique using a lower rotation speed when a physician wants to move an atherectomy catheter on a guide wire (e.g., to prevent disturbance or damage to tissue), is eliminated with the fluid bearings as described herein. The fluid bearings provide a fluid interface between the guide wire lumen of the drive shaft and the liner (or alternatively between the drive shaft and the guide wire if no liner is present) to accordingly facilitate the sliding exchange of a guide wire relative to the catheter. In another example, a dedicated guide wire liner is self-priming with the guide wire by penetrating an orifice at a point along the guide wire liner so high pressure fluid (e.g., saline, lubricant, and/or medicament) bleeds through the orifice to continually fill the ID of the guide wire liner with saline and/or lubricant, such as Rotaglide® or Viperslide®. The orifice is optionally located near a distal portion of the catheter (e.g., distal to the drive shaft) to minimize risk of a structural failure of a non-rotatable feature. In other words, any failure would occur distally of the drive shaft and accordingly not result in seizing and transmission of rotation to the guide wire.

Further still, a catheter including a septum in the catheter body that divides the infusion and aspiration lumens is more efficient with regard to infusion aspiration capacities because the resulting dual lumens (divided by the septum) provide additional cross sectional area for each lumen relative to a corresponding catheter having coaxial lumens (e.g., an infusion tube within an aspiration lumen or the converse). Additional efficiencies are realized because movement of the higher viscosity particulate entrained effluent (relative to just the infusion fluid) is not resisted by rotation of the drive shaft. Instead, the effluent is isolated from the rotating drive shaft and accordingly free to move along the catheter body without rotational resistance from the drive shaft. Similarly, the drive shaft is not slowed by passage of the effluent including the entrained particulate. Instead, the drive shaft is bathed by the infusion fluid in the infusion lumen, and the infusion fluid has a lower viscosity and that accordingly minimizes rotational resistance for the drive shaft. In this manner the energy supplied and consumed by a catheter incorporating these features is conserved and optimally used (e.g., for the provision of rotation, infusion and aspiration).

In another example, the dual lumen catheter body includes the septum spanning the catheter body. The catheter body including the septum provides greater structural integrity provides enhanced pushability. Furthermore, the structural integrity is realized in a cost effective fashion as the catheter body is extruded from polymer and optionally includes a braid, as opposed to a laser cut tube. Expensive and labor intensive inner and outer sheaths are accordingly avoided.

Furthermore, providing a dual lumen tube negates the possible pinching effect encountered with sheaths in existing devices which can close off infusion fluid being delivered to the distal tip of the device, and in certain circumstances may lead to ballooning of the outer sheath and possible burst of the weakened area.

Figure 3:
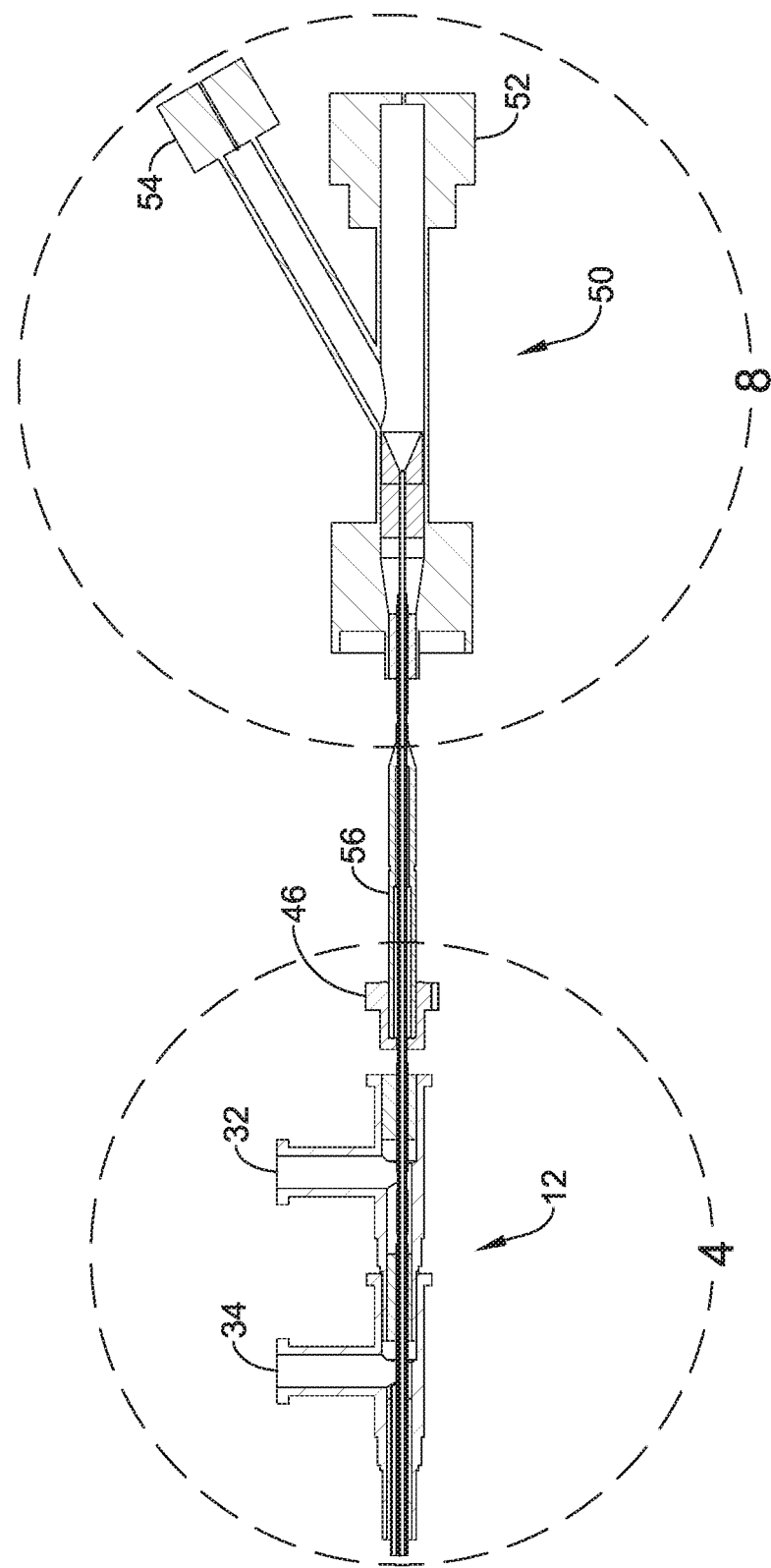
FIG. 3 is a longitudinal cross-sectional view of the proximal end region of the exemplary matter elimination catheter of FIG. 1.

Now referring to FIG. 1 and the associated cross-sectional view of FIG. 3, there is illustrated a proximal end region of an exemplary matter elimination catheter 10. The proximal end region of the catheter 10 may include a manifold 12 attached to a proximal end of an elongate shaft 14, with the elongate shaft 14 extending distally therefrom.

The elongate shaft 14 may include a catheter body 16 having a proximal end extending into and secured to the manifold 12. For example, a bond region 18 between the catheter body 16 and the manifold 12, shown in FIG. 2, may secure the catheter body 16 to the manifold 12. For example, proximal end of the catheter body 16 may be adhesively bonded, thermally bonded, mechanically coupled or otherwise secured to the manifold at the bond region 18.

Figure 2:
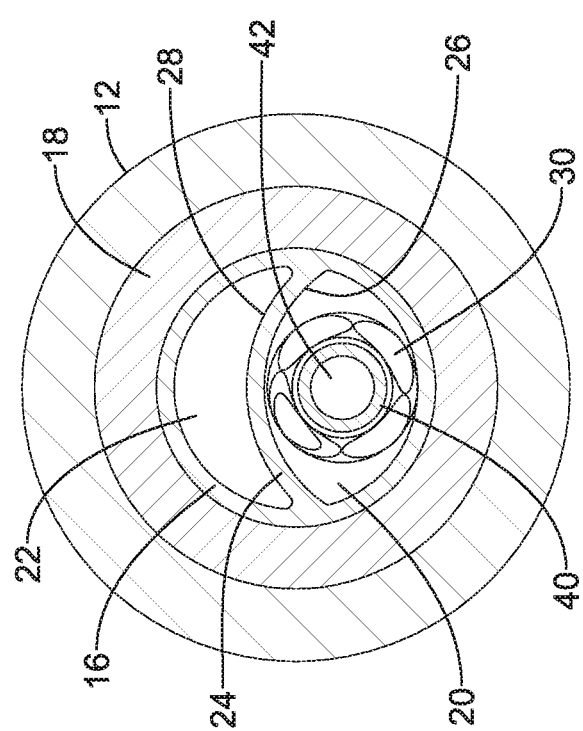
FIG. 2 is a transverse cross-sectional view of the matter elimination catheter taken along line 2-2 of FIG. 1.

The catheter body 16 may include one or more, or a plurality of lumens extending therethrough. For example, the catheter body 16 may include an infusion lumen and an aspiration lumen fluidly isolated from the infusion lumen, as well as one or more additional lumens, if desired. As shown in FIG. 2, in some instances the catheter body 16 may be a dual lumen extruded tubular member defining an infusion lumen 20 and an aspiration lumen 22 fluidly isolated from the infusion lumen 20. Thus, the catheter body 16 may be a monolithic structure including both an infusion lumen 20 and an aspiration lumen 22 extending therethrough.

The catheter body 16 may include a septum 24 spanning across the catheter body 16 to divide the interior space of the catheter body 16 into infusion lumen 20 and the aspiration lumen 22. For example, the septum 24 may span from the annular outer wall of the catheter body 16 on one side of the catheter body 16 to the annular outer wall of the catheter body 16 on an opposite side of the catheter body 16. Thus, a first surface 26 of the septum 24 may partially define the infusion lumen 20 along with a first portion of the inner surface of the annular outer wall of the catheter body 16, while a second surface 28 of the septum 24 may partially define the aspiration lumen 22 along with a second portion of the inner surface of the annular outer wall of the catheter body 16.

In some instances, as shown in FIG. 2, the septum 24 may have a bowed or arcuate configuration such that one of the first and second surfaces 26, 28 of the septum 24 is convex while the other of the first and second surfaces 26, 28 of the septum 24 is concave. For example, the first surface 26 of the septum 24 may be concave such that the infusion lumen 20 may have a generally elliptical or oval shape, while the second surface 28 of the septum 24 may be convex such that the aspiration lumen 22 may have a generally crescent shape. In other embodiments, the curvature of the septum 24 may be reversed, in which case the shapes of the infusion lumen 20 and the aspiration lumen 22 may also be reversed. In yet other embodiments, the septum 24 may be planar, with opposing flat surfaces.

Figure 4:
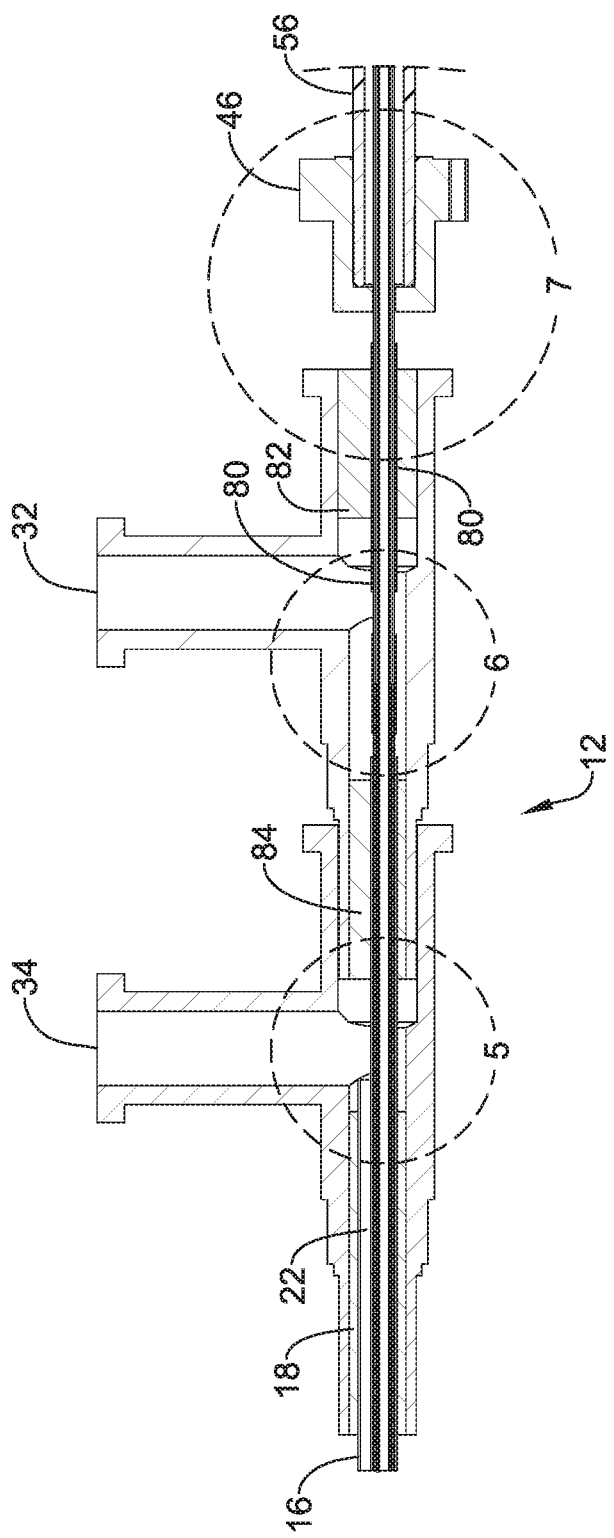
FIG. 4 is an enlarged view of a portion of the matter elimination catheter shown in FIG. 3.
Figure 5:
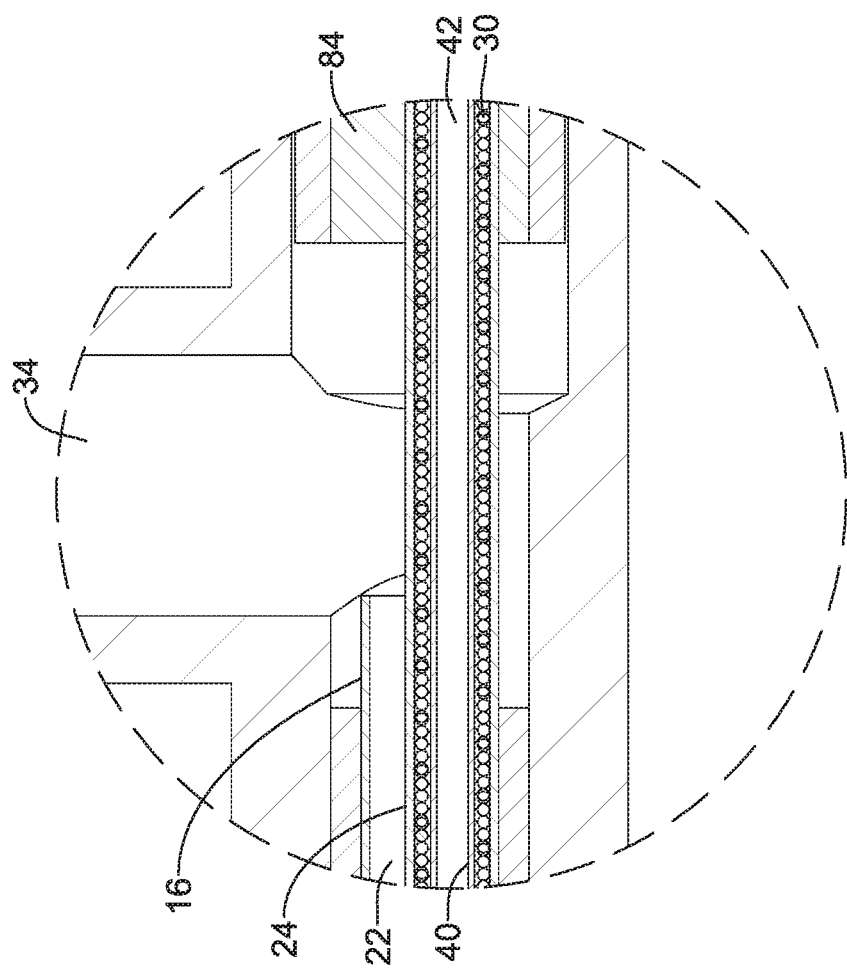
FIG. 5 is an enlarged view of a portion of the matter elimination catheter shown in FIG. 4.

Referring to FIGS. 4 and 5, the manifold 12 may include an infusion port 32 in fluid communication with the infusion lumen 20 for delivering an infusion fluid through the infusion lumen 20 to the distal end of the elongate shaft 14. In some instances, a first Y-adapter may provide the infusion port 32. A source of infusion fluid may be coupled to the infusion port 32 during operation of the catheter 10.

Figure 6:
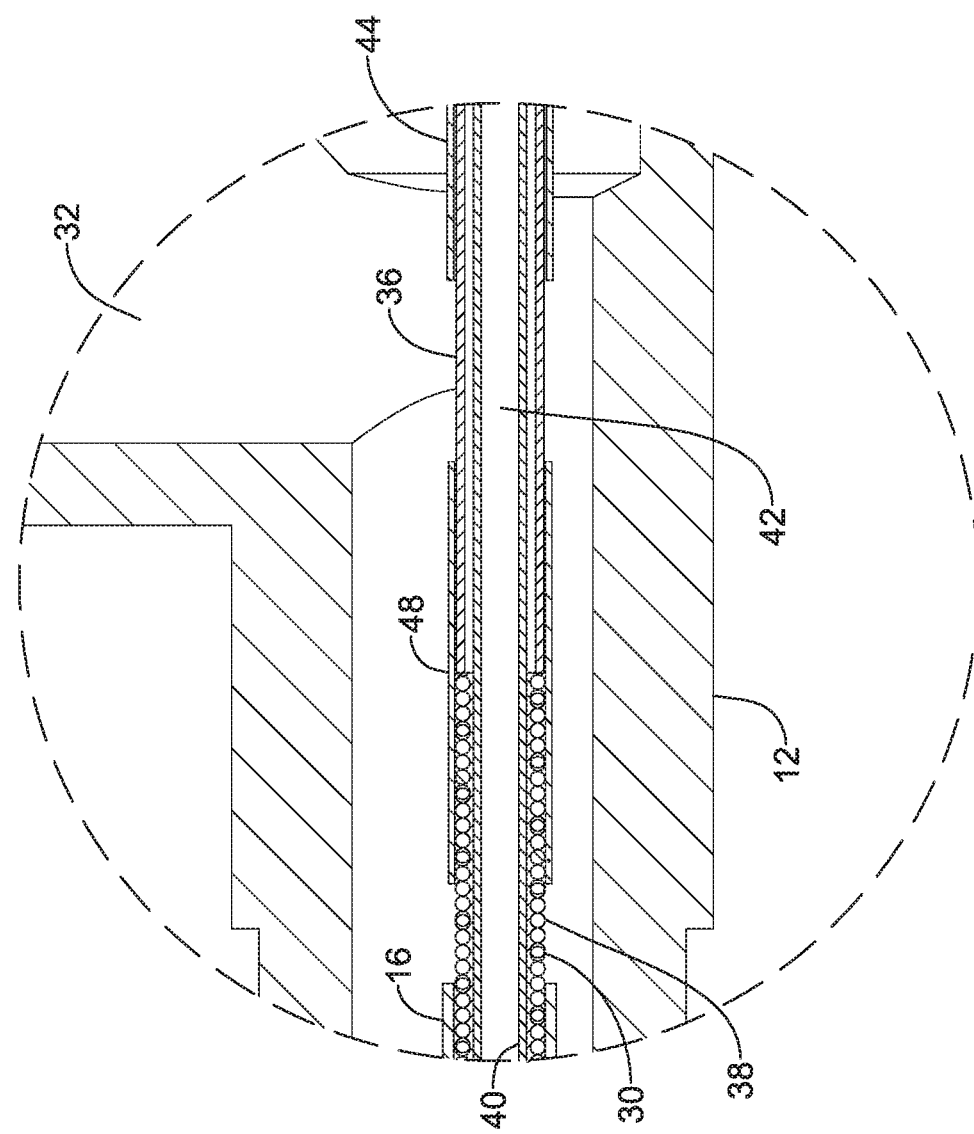
FIG. 6 is an enlarged view of a portion of the matter elimination catheter shown in FIG. 4.

Referring to FIGS. 4 and 6, the manifold 12 may also include an aspiration port 34 in fluid communication with the aspiration lumen 22 for withdrawing effluent through the aspiration lumen 22 from the distal end of the elongate shaft 14. For example, a proximal portion of the catheter body 16 within the manifold 12 may be skived to provide a fluid pathway between the aspiration lumen 22 and the aspiration port 34, leaving the septum 24 and portion of the catheter body 16 defining the infusion lumen 20 extending further proximal of the aspiration port 34. The septum 24 and portion of the catheter body 16 defining the infusion lumen 20 proximal of the aspiration port 34 may be secured to the manifold 12 at a bond location 84 proximal of the aspiration port 34 and the aspiration lumen 22. The bond location 84 may isolate infusion fluid entering the infusion lumen 20 of the catheter body 16 through the infusion port 32 from effluent exiting the aspiration lumen 22 of the catheter body 16 through the aspiration port 34. In some instances, a second Y-adapter may provide the aspiration port 34. A vacuum source may be coupled to the aspiration port 34 during operation of the catheter 10 to draw a vacuum through the aspiration lumen 22.

As shown in FIGS. 2, 3 and 4, the elongate shaft 14 may also include a drive shaft 30 extending through a lumen of the catheter body 16. For example, the drive shaft 30 may extend through the infusion lumen 20, and thus be isolated from the aspiration lumen 22 and effluent passing through the aspiration lumen 22. In some instances, the drive shaft 30, or a portion thereof, may include a coiled member formed of one or more tight wound filaments and/or a solid-walled tubular member. In some instances, a proximal portion of the drive shaft 30 may be formed of a solid-walled tubular member 36 and a distal portion of the drive shaft 30 may be formed of a coiled member 38 secured to the solid-walled tubular member 36, as shown in FIG. 6. For instance, a proximal end of the coiled member 38 may be secured to a distal end of the solid-walled tubular member 36 at a joint, such as a butt joint, or a lap joint (e.g., the proximal end of the coiled member 38 may extend into the lumen of the solid-walled tubular member 36, or vice versa). In some instances, a sleeve 48 may extend across the joint, surrounding both the proximal end of the coiled member 38 and the distal end of the solid-walled tubular member 36, and secured thereto. The sleeve 48 may extend along any length of the coiled member 38 and/or the solid-walled tubular member 36, as desired.

The drive shaft 30 may be rotatable and/or axially translatable within the infusion lumen 20 of the catheter body 16. For example, the matter elimination catheter 10 may include a prime mover (not shown) to provide rotational motion to the drive shaft 30 to rotate a cutting member positioned at the distal end of the elongate shaft 14. For example, in some instances the prime mover may be an electrical motor, a fluid turbine, or the like. A controller (not shown) may be used to control the prime mover. For example, the user may provide power to the prime mover and/or control the speed of rotation of the drive shaft 30 via a controller. In the illustrated embodiment, a pinion gear 46 may be secured to the drive shaft 30 to transfer rotational motion from the prime mover to the drive shaft 30. For example, the pinion gear 46 may be secured to a pinion shaft 56, which is secured to the drive shaft 30 such that rotation of the pinion gear 46 and pinion shaft 56 causes rotation of the drive shaft 30 within the catheter body 16.

In some embodiments, the lumen of the drive shaft 30 may define the guide wire lumen 42 extending through the drive shaft 30. However, in other embodiments, a guide wire liner 40 may extend through the lumen of the drive shaft 30 to define the guide wire lumen 42, as shown in the illustrated embodiment. The guide wire liner 40 may be a thin walled tubular member creating an interface between the inner surface of the drive shaft 30 and the guide wire extending through the guide wire lumen 42. The guide wire liner 40 may be positioned with the lumen of the drive shaft 30 such that the guide wire liner 40 remains stationary as the drive shaft 30 rotates during operation of the catheter 10. Accordingly, there is no relative rotational movement between the guide wire and the component directly surrounding the guide wire (e.g., the guide wire liner 40) during operation of the catheter 10. As shown in the illustrated embodiment, the guide wire liner 40 may extend the entire length of the drive shaft 30, and may extend proximal of the proximal end of the drive shaft 30 and/or may extend distal of the distal end of the drive shaft 30.

Figure 7:
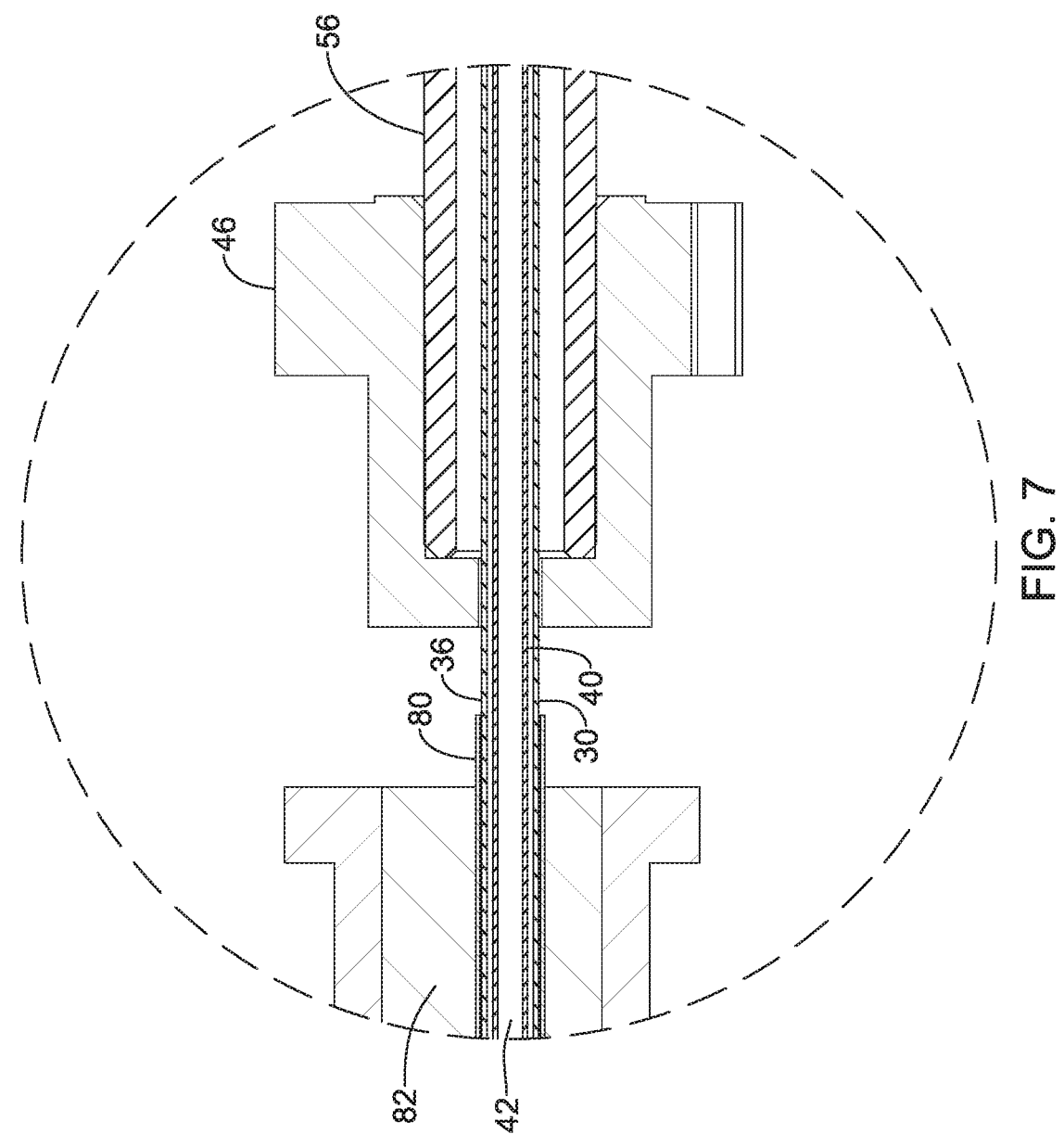
FIG. 7 is an enlarged view of a portion of the matter elimination catheter shown in FIG. 4.

The drive shaft 30, such as the solid-walled tubular member 36 (e.g., a stainless steel hypotube), may extend into and/or through a distal seal tube 80, shown in FIGS. 4, 6 and 7. The distal seal tube 80 may be a polymeric tubular member, such as a polyimide tubular member, in some instances. The distal seal tube 80 may be secured to the manifold 12 at a bond location 82. Accordingly, the drive shaft 30 may be rotatable relative to the distal seal tube 80 and the manifold 12. A tight tolerance may be maintained between the outer surface of the drive shaft 30 and the inner surface of the distal seal tube 80 to provide a hydraulic seal therebetween. Thus, infusion fluid introduced through the infusion port 32 may not escape and/or air may not enter through the clearance between the drive shaft 30 and the distal seal tube 80.

Figure 8:
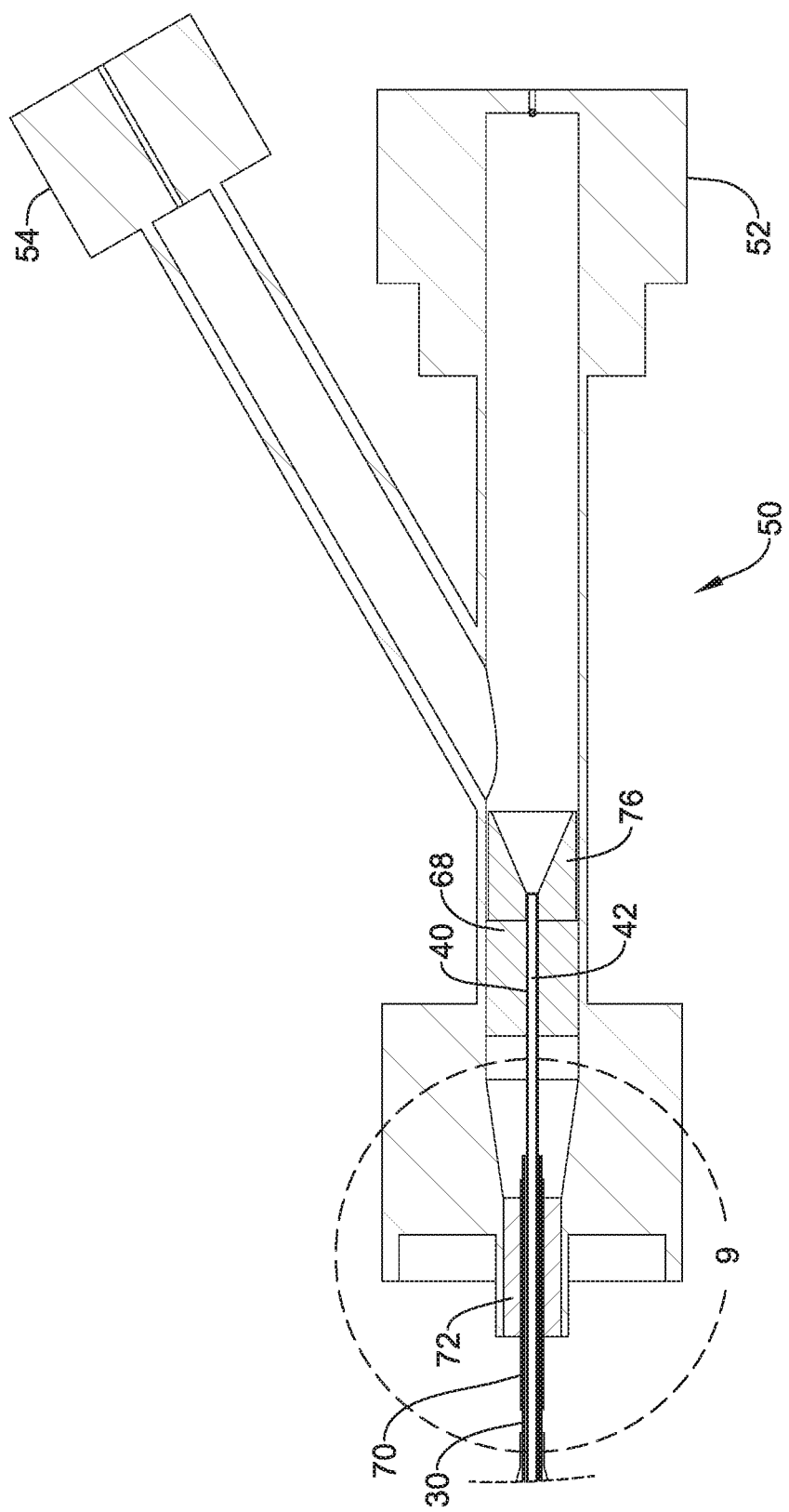
FIG. 8 is an enlarged view of a portion of the matter elimination catheter shown in FIG. 3.

As shown in FIG. 8, the catheter 10 may also include an adapter 50, such as a Tuohy-Borst adapter, coupled to a proximal end of the drive shaft 30 and/or guide wire liner 40, if present. For instance, the proximal end of the drive shaft 30 and/or the proximal end of the guide wire liner 40 may extend into the adapter 50. As shown, the guide wire liner 40 may extend proximal of the proximal end of the drive shaft 30 and be secured to the adapter 50 at a bond location 68. The adapter 50 may include a guide wire port 52 providing guide wire access to the guide wire lumen 42. The adapter 50 may also include a side or auxiliary access port 54 for access to the guide wire lumen 42.

The adapter 50 may include a guide wire director 76 to facilitate positioning a guide wire into the guide wire lumen 42. For example, the guide wire director 76 may include a tapered or conical bore arranged to direct a guide wire into the guide wire lumen 42. Although not shown, the adapter 50 may include a hemostasis valve to create a fluid seal around a guide wire inserted into the guide wire lumen 42.

Figure 9:
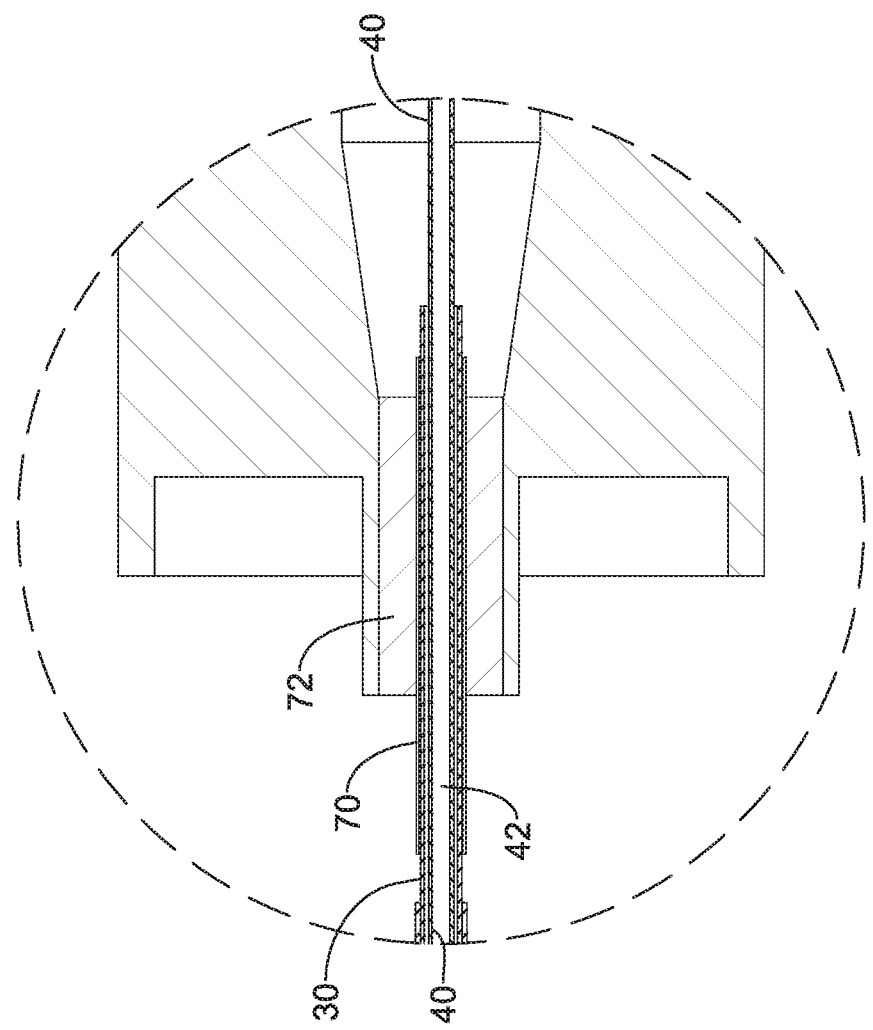
FIG. 9 is an enlarged view of a portion of the matter elimination catheter shown in FIG. 8.

Furthermore, the drive shaft 30, such as the solid-walled tubular member 36, may extend into and/or through a proximal seal tube 70, shown in FIG. 9. The proximal seal tube 70 may be a polymeric tubular member, such as a polyimide tubular member, in some instances. The proximal seal tube 70 may be secured to the adapter 50 at a bond location 72. Accordingly, the drive shaft 30 may be rotatable relative to the proximal seal tube 70 and the adapter 50. A tight tolerance may be maintained between the outer surface of the drive shaft 30 and the inner surface of the proximal seal tube 70 to provide a hydraulic seal therebetween.

In some instances, the proximal seal tube 70, or another tubular member surrounding the drive shaft 30, may serve as a diversion sleeve for diverting infusion fluid distally along the drive shaft 30. The proximal seal tube 70 (or other tubular member), which may extend proximally relative to the infusion port 32, may extend along the drive shaft 30 for a distance distal of the infusion port 32. In some instances, the proximal seal tube 70 (or other tubular member) serving as a diversion sleeve may extend along the drive shaft 30 distal of the infusion port 32 any desired length, such as about 1 inch (2.54 cm) or less, about 2 inches (5.08 cm) or less, about 3 inches (7.62 cm) or less, or about 4 inches (10.16 cm) or less, although other lengths may also be used. Accordingly, infusion fluid introduced through the infusion port 32 may be directed distally over an exterior perimeter of the diversion sleeve (e.g., the proximal seal tube 70) up to the distal end of the diversion sleeve, at which point a first portion of the infusion fluid flows distally through the infusion lumen 20 toward the distal end region of the catheter 10 and a second portion of the infusion fluid flows proximally along an interior perimeter of the diversion sleeve (e.g., the proximal seal tube 70) between the drive shaft 30 and the diversion sleeve (e.g., the proximal seal tube 70). The distribution of infusion fluid between the first and second portions may be controlled by the length of the diversion sleeve distal of the infusion port 32 and/or the dimensions (e.g., tolerance) between the inner diameter of the diversion sleeve and the outer diameter of the drive shaft 30. The first portion of the infusion fluid may provide a fluid bearing between a guide wire or the guide wire liner 40 and the drive shaft 30, while the second portion of infusion fluid may provide a fluid bearing between the drive shaft 30 and the diversion sleeve (e.g., the proximal seal tube 70).

In some instances, the manifold 12, including the infusion port 32 and the aspiration port 34, may be considered a distal manifold assembly and the adapter 50, providing the guide wire port 52, may be considered a proximal manifold assembly. The pinion gear 46 and pinion shaft 56 may be positioned between the distal manifold assembly (e.g., manifold 12) and the proximal manifold assembly (e.g., adapter 50), and rotatable relative to both the manifold 12 and the adapter 50.

Figure 10:
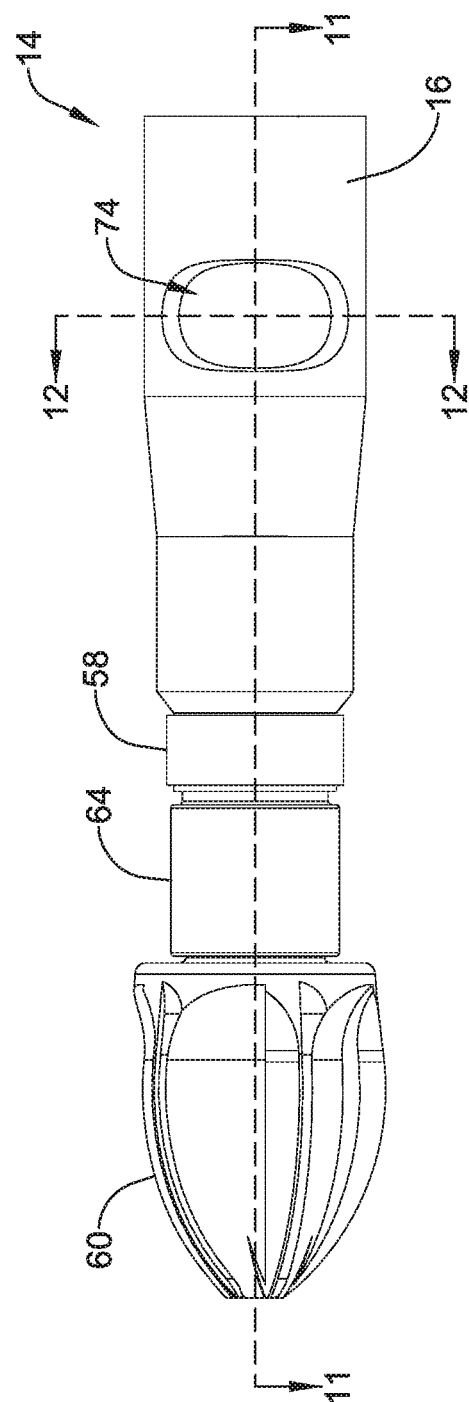
FIG. 10 is a side plan view of a distal end region of an exemplary matter elimination catheter in accordance with this disclosure.
Figure 11:
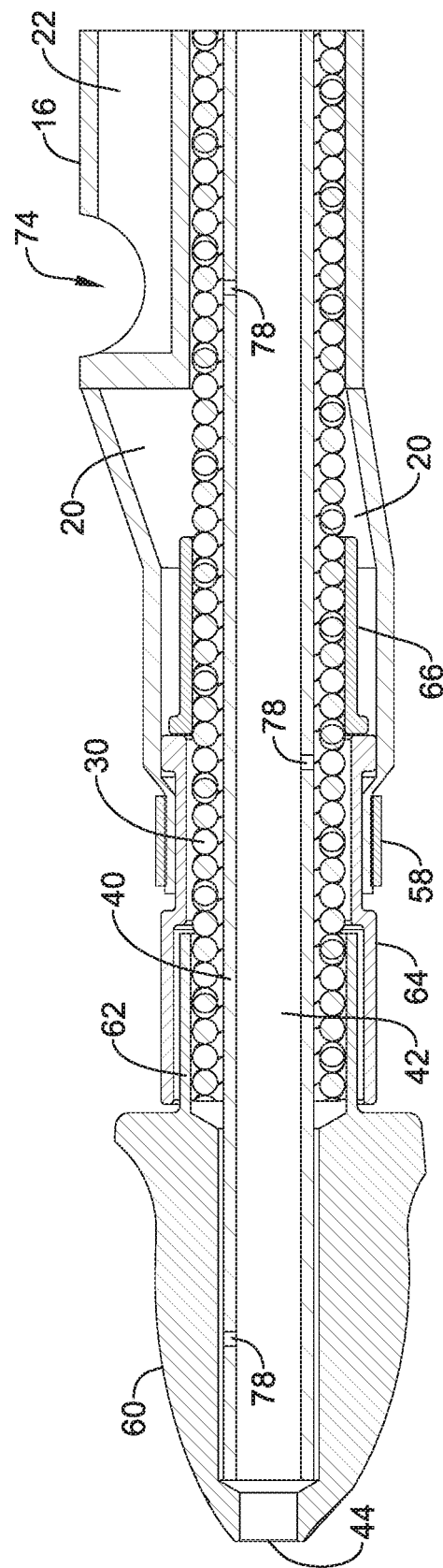
FIG. 11 is a longitudinal cross-sectional view of the distal end region of the exemplary matter elimination catheter of FIG. 10 taken along line 11-11 of FIG. 10.

An exemplary distal end region of the catheter 10 is illustrated at FIGS. 10 and 11. The distal end region of the catheter 10 may include a rotatable cutting member 60 positioned at the distal end of the elongate shaft 14. The cutting member 60 may be secured to the distal end of the drive shaft 30, and thus rotated through rotation of the drive shaft 30. For example, the distal end of the drive shaft 30 may extend into a bore of a proximal neck 62 of the cutting member 60 and be fixedly secured thereto, such as by welding, adhesive, interference fit, or the like. The cutting member 60 may include one or more flutes having a cutting edge for removing occlusive material from a body lumen. In other instances, the cutting member 60 may be a burr having an abrasive surface, such as a diamond coated abrasive surface, or the cutting member 60 may be of another construction for abrading or cutting occlusive material. In some instances, the cutting member 60 may be positioned distal of the catheter body 16. In other instances, the cutting member 60, or a portion thereof, may be positioned within the distal end region of the catheter body 16, if desired.

In some instances, the cutting member 60 may be rotatably coupled to the catheter body 16. For example, as shown in FIGS. 10 and 11, a coupling assembly may be provided at the distal end region of the elongate shaft 14 to permit rotation between the cutting member 60/drive shaft 30 and the catheter body 16. For example, the coupling assembly may include a saddle 64 at the distal end of the catheter body 16 and a retaining ring 66 secured to the drive shaft 30. The saddle 64 may be an integral portion of the catheter body 16, or a separate component secured thereto. The saddle 64 may be fixedly secured to the distal end of the catheter body 16 by welding, crimping, adhesive, interference fit, or the lit. Similarly, the retaining ring 66 may be fixedly secured to the drive shaft 30, such as the outer surface of the drive shaft 30, by welding, crimping, adhesive, interference fit, or the like. The saddle 64 and the retaining ring 66 may be formed of any desired material, such as stainless steel, titanium, tungsten, or other metallic material, although polymeric or ceramic materials, as well as other materials may also be used if desired. The saddle 64 may be configured to constrain proximal and distal movement of the cutting member 60 relative to the catheter body 16 while permitting rotational movement of the cutting member 60 relative to the catheter body 16. For example, the neck portion 62 of the cutting member 60 may extend into the saddle 64 such that a stop surface of the neck portion 62 engages with a stop surface (e.g., distal flange) of the saddle 64 to inhibit proximal movement of the cutting member 60 relative to the catheter body 16. In some instances, the saddle 64 may serve as a guide or bearing to maintain alignment between the cutting member 60 and the catheter body 16. Furthermore, the retaining ring 66 may be fixedly secured to the drive shaft 30 proximal of the saddle 64 such that a stop surface of the retaining ring 66 engages with a stop surface (e.g., proximal flange) of the saddle 64 to inhibit distal movement of the drive shaft 30, and thus the cutting member 60, relative to the catheter body 16.

The saddle 64 may be fixedly secured to the catheter body 16 in any desired way. For example, the saddle 64 may be adhesively bonded and/or mechanically engaged to the catheter body 16. In the illustrative embodiment, a radiopaque marker ring 58 may be crimped around a portion of the catheter body 16 overlaying a reduced diameter portion (e.g., an annular groove) of the saddle 64 to secure the catheter body 16 to the saddle 64.

The cutting member 60 may include a distal opening 44 aligned with the guide wire lumen 42 to permit a guide wire to pass therethrough into the guide wire lumen 42. The guide wire liner 40, if present, may extend through the drive shaft 30 to define the guide wire lumen 42. The guide wire liner 40 may extend distal of the distal end of the drive shaft 30 into the bore of the cutting member 60 to form an interface between the cutting member 60 and a guide wire extending through the guide wire lumen 42. The bore of the cutting member 60 may have a diameter slightly larger than the outer diameter of the guide wire liner 40 to provide a clearance for infusion fluid to pass therebetween to lubricate the guide wire, as will be further discussed herein. The guide wire liner 40 may remain stationary as the cutting member 60 is rotated. Thus, the cutting member 60 is rotatable relative to the guide wire liner 40 during operation, such that the guide wire is isolated from direct contact with the rotating cutting member 60 except at the distal opening 44 of the cutting member 60.

Figure 12:
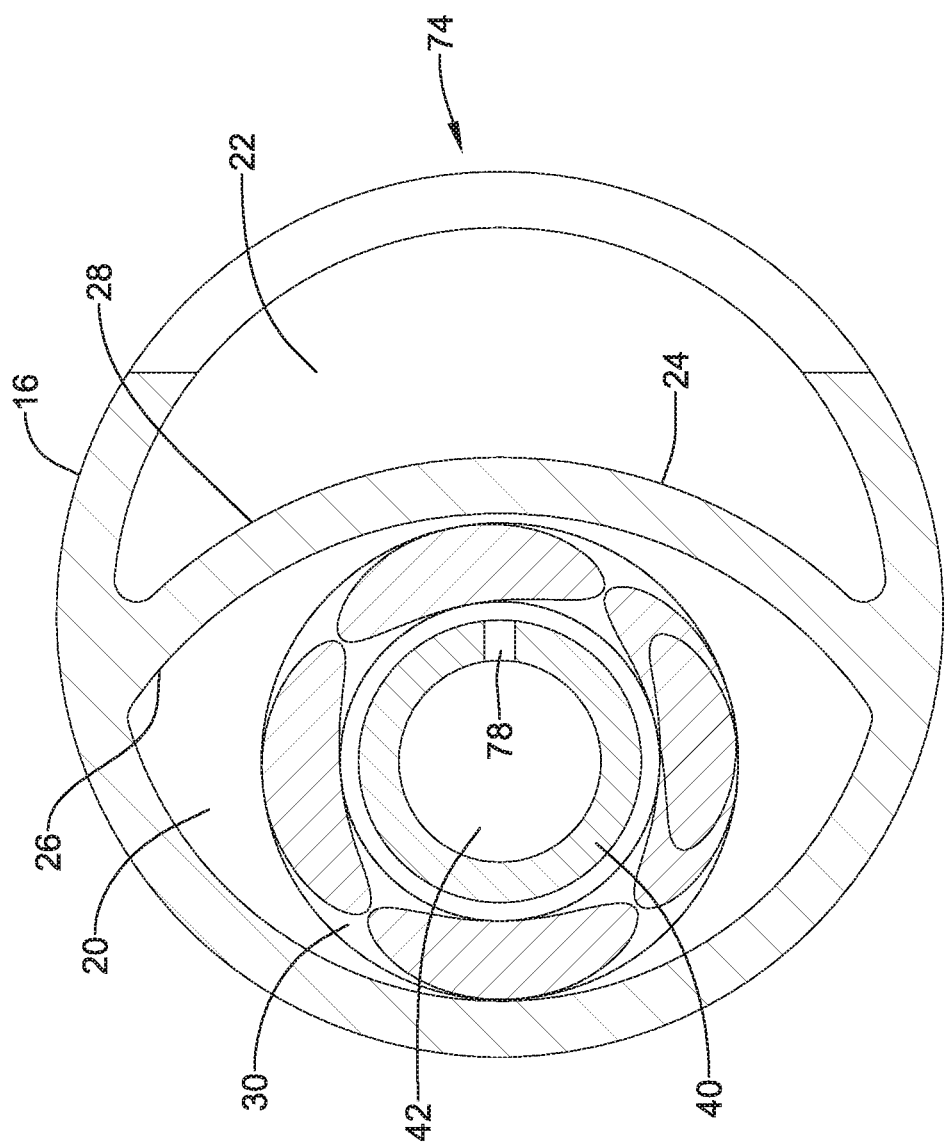
FIG. 12 is a transverse cross-sectional view of the matter elimination catheter taken along line 12-12 of FIG. 10.

The distal end region of the elongate shaft 14 may include one or more, or a plurality of aspiration or inflow ports for aspirating effluent into the aspiration lumen 22 of the catheter body 16. For example, the distal end region of the catheter body 16 may include an inflow port 74 opening into the aspiration lumen 22. As shown in FIG. 12, the inflow port 74 may open into the aspiration lumen 22 through a sidewall of the catheter body 16. The septum 24 may isolate the drive shaft 30, extending through the infusion lumen 20 from effluent passing into the aspiration lumen 22. Furthermore, FIG. 12 illustrates that within the distal end region, the septum 24 may have a bowed or arcuate configuration such that one of the first and second surfaces 26, 28 of the septum 24 is convex while the other of the first and second surfaces 26, 28 of the septum 24 is concave. For example, the first surface 26 of the septum 24 may be concave such that the infusion lumen 20 may have a generally elliptical or oval shape, while the second surface 28 of the septum 24 may be convex such that the aspiration lumen 22 may have a generally crescent shape. In other embodiments, the curvature of the septum 24 may be reversed, in which case the shapes of the infusion lumen 20 and the aspiration lumen 22 may also be reversed. In yet other embodiments, the septum 24 may be planar, with opposing flat surfaces.

Figure 13:
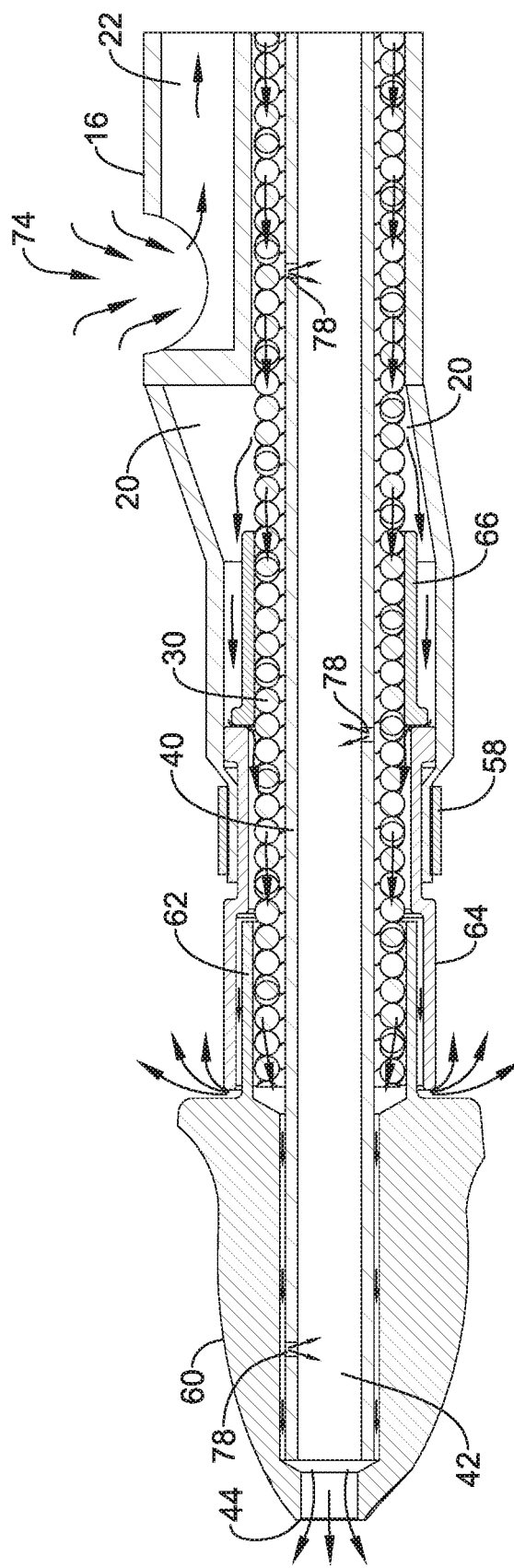
FIG. 13 is a cross-sectional view illustrating exemplary flows through the distal end region of the exemplary matter elimination catheter of FIG. 11.

FIG. 13 illustrates exemplary flow paths of an infusion fluid and an effluent at the distal end region of the catheter 10 shown in FIG. 11. A pressurized infusion fluid (e.g., saline, Rotoglide, etc.), from an infusion fluid source (e.g., saline bag, etc.) in fluid communication with the infusion lumen 20, may pass through the infusion lumen 20 and be in direct contact with the drive shaft 30. In some instances, the infusion fluid may penetrate between adjacent coils of the drive shaft 30 such that infusion fluid is located within the lumen of the drive shaft 30, such as between the outer surface of the guide wire liner 40 and the inner surface of the drive shaft 30, or between the outer surface of a guide wire and the inner surface of the drive shaft 30 (when no guide wire liner 40 is present), as well as along an exterior of the drive shaft 30 (i.e., between the outer surface of the drive shaft 30 and the inner surface of the infusion lumen 20. In some instances, the infusion fluid may provide one or more fluid bearings between components of the catheter 10. The fluid bearings may be fluid dynamic bearings or hydrostatic bearings, for example.

The pressurized infusion fluid through the infusion lumen 20 interposed between the drive shaft 30 and the catheter body 16 may form a shaft fluid bearing between the drive shaft 30 and the catheter body 16 (i.e., between the outer surface of the drive shaft 30 and the inner surface of the infusion lumen 20). The shaft fluid bearing may extend from the catheter proximal portion near the manifold 12 to the catheter distal portion near the distal end of the drive shaft 30. For example, the shaft fluid bearing may extend along the length of the drive shaft 30.

The pressurized infusion fluid through the infusion lumen 20 interposed between the guide wire liner 40 or a guide wire in the guide wire lumen 42 and the drive shaft 30 may form a guide wire fluid bearing between the outer surface of the guide wire liner 40 or a guide wire and the inner surface of the drive shaft 30. The guide wire fluid bearing may extend from the catheter proximal portion near the manifold 12 to the catheter distal portion near the distal end of the drive shaft 30. For example, the guide wire fluid bearing may extend along the length of the drive shaft 30.

The infusion fluid may exit the distal end region of the catheter 10 at one or more outflow ports. For example, as shown with the arrows in FIG. 13, infusion fluid may pass through a clearance gap between the outer surface of the guide wire liner 40 and the inner surface of the bore through the cutting member 60 and out the distal opening 44. Additionally or alternatively, infusion fluid may pass between the retaining ring 66 and the catheter body 16, between the retaining ring 66 and the saddle 64, between the saddle 64 and the drive shaft 30 and/or between the cutting member 60 (e.g., the neck 62) and the saddle 64, and exit through a clearance gap between the cutting member 60 and the saddle 64. The pressurized infusion fluid may form a fluid bearing between one or more of these structures, such as between one or more of the guide wire liner 40, guide wire, cutting member 60, saddle 64, retaining ring 66, drive shaft 30, and catheter body 16. For example, pressurized fluid through the infusion lumen 20 interposed between the cutting member 60 and the catheter body 16 (e.g., saddle 64) may form a cutter fluid bearing between the cutting member 60 (e.g., neck 62) and the catheter body 16 (e.g., saddle 64)), and/or pressurized fluid through the infusion lumen 20 interposed between the cutting member 60 and the guide wire liner 40 or guide wire may form a cutter fluid bearing between the cutting member 60 and the guide wire liner 40 or guide wire extending through the bore of the cutting member 60.

In some instances, such as shown in FIGS. 11-13, the guide wire liner 40 may include one or more, or a plurality of orifices 78 extending through the sidewall of the guidewire liner 40. Although three orifices 78 are shown, in other embodiments the guide wire liner 40 may include one, two, four, five, or more orifices arranged at any desired location along the guide wire liner 40. The orifice(s) may be provided so high pressure fluid (e.g., saline, lubricant, and/or medicament) within the infusion lumen 20 passes (e.g., weeps, oozes, drips, sprays, bleeds, etc.) through the orifice 78 to continually fill the lumen of the guide wire liner 40 with saline and/or lubricant, such as Rotoglide. Arrows shown in FIG. 13 illustrate infusion fluid passing through the orifices 78 into the guide wire lumen 42 defined by the guide wire liner 40. Infusion fluid passing into the lumen of the guide wire liner 40 may help lubricate the guide wire extending therethrough, for example. One or more of the orifices 78 may optionally be located near a distal portion of the catheter 10 (e.g., distal to the drive shaft 30 and/or within the bore of the cutting member 60).

Furthermore, the pressurized infusion fluid may provide a fluid barrier to prevent ingress of effluent, including particulates such as fibrin, from entering the distal end region of the catheter 10 through the distal opening 44, between the outer surface of the guide wire liner 40 and the inner surface of the bore through the cutting member 60, between the cutting member 60 (e.g., the neck 62) and the saddle 64 or other clearance gap between one or more of the guide wire liner 40, guide wire, cutting member 60, saddle 64, retaining ring 66, drive shaft 30, and catheter body 16. In other words, the pressure gradient between the pressurized infusion fluid within the distal end region of the catheter 10 and the pressure within the body lumen may permit infusion fluid to exit through one or more of these pathways, while preventing effluent to enter the distal end region of the catheter 10 through one or more of these pathways.

Also shown in FIG. 13, a vacuum may be drawn through the aspiration lumen 22 via an aspiration source (e.g., pump) in communication with the aspiration lumen 22 to draw effluent (e.g., infusion fluid and entrained particulates) into the aspiration lumen 22 through the aspiration or inflow port 74. The effluent is isolated from the drive shaft 30 via the septum 24. Therefore, the drive shaft 30 may be continuously covered with the infusion fluid, while not being fouled with particulates from the effluent.

Figure 14:
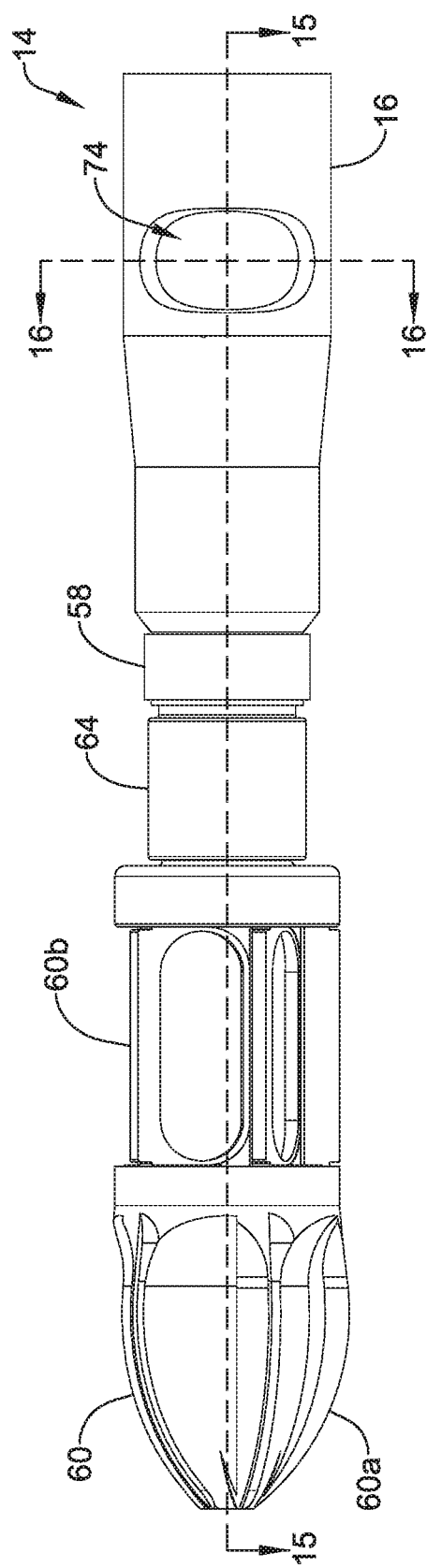
FIG. 14 is a side plan view of an alternative distal end region of an exemplary matter elimination catheter in accordance with this disclosure.
Figure 15:
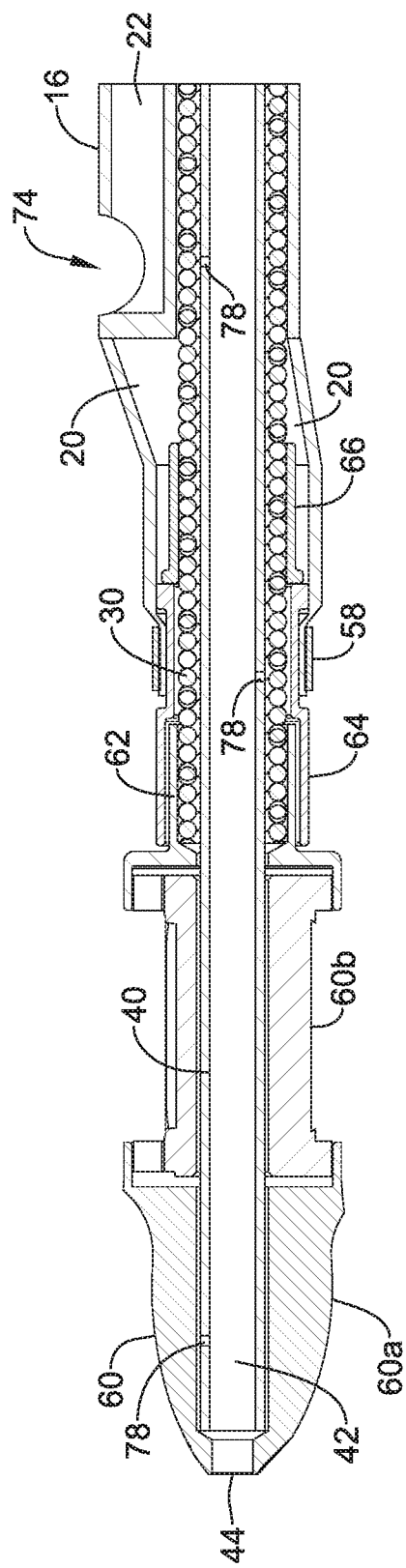
FIG. 15 is a longitudinal cross-sectional view of the distal end region of the exemplary matter elimination catheter of FIG. 14 taken along line 15-15 of FIG. 14.

An alternative distal end region of the catheter 10 is illustrated at FIGS. 14 and 15. The distal end region shown in FIGS. 14 and 15 may be similar to the distal end region of the catheter 10 shown in FIGS. 10 and 11 in many respects, with the exception of features noted below. For instance, the cutting member 60 may be rotatably coupled to the catheter body 16 via a coupling assembly provided at the distal end region of the elongate shaft 14 to permit rotation between the cutting member 60/drive shaft 30 and the catheter body 16. For example, the coupling assembly may include a saddle 64 at the distal end of the catheter body 16 and a retaining ring 66 secured to the drive shaft 30. Additionally, the cutting member 60 may include a distal opening 44 aligned with the guide wire lumen 42 to permit a guide wire to pass therethrough into the guide wire lumen 42. The guide wire liner 40, if present, may extend through the drive shaft 30 to define the guide wire lumen 42. The guide wire liner 40 may extend distal of the distal end of the drive shaft 30 into the bore of the cutting member 60 to form an interface between the cutting member 60 and a guide wire extending through the guide wire lumen 42. The bore of the cutting member 60 may have a diameter slightly larger than the outer diameter of the guide wire liner 40 to provide a clearance for infusion fluid to pass therebetween to lubricate the guide wire, as will be further discussed herein. The guide wire liner 40 may remain stationary as the cutting member 60 is rotated. Thus, the cutting member 60 is rotatable relative to the guide wire liner 40 during operation, such that the guide wire is isolated from direct contact with the rotating cutting member 60 except at the distal opening 44 of the cutting member 60. Further discussion of the similar features, and their interaction with other components has been described above, and thus will not be repeated.

The distal end region of the catheter 10 shown in FIGS. 14 and 15 may include a rotatable cutting member 60 having a distal cutter 60a and a proximal cutter 60b. Both the distal cutter 60a and the proximal cutter 60b may be rotated through rotation of the drive shaft 30. The distal cutter 60a may include one or more flutes having a cutting edge for removing occlusive material from a body lumen. In other instances, the distal cutter 60a may be a burr having an abrasive surface, such as a diamond coated abrasive surface, or the distal cutter 60a may be of another construction for abrading or cutting occlusive material. The proximal cutter 60b may be an expandable cutter including one or more expandable blades, or the proximal cutter 60b may be a morcellator or macerator for morcellating or macerating excised tissue, for example. In some instances, the proximal cutter 60b may have a first cutting diameter when the drive shaft 30 is rotated in a first rotational direction (e.g., clockwise) and a second cutting diameter when the drive shaft 30 is rotated in an opposite, second rotational direction (e.g., counter-clockwise. The first cutting diameter may be different than the second cutting diameter, for example, the first cutting diameter may be less than the second cutting diameter. For instances, the blades of the proximal cutter 60b may expand to the second cutting diameter or beyond from the first cutting diameter when the drive shaft 30 is rotated in the second rotational direction.

Figure 16:
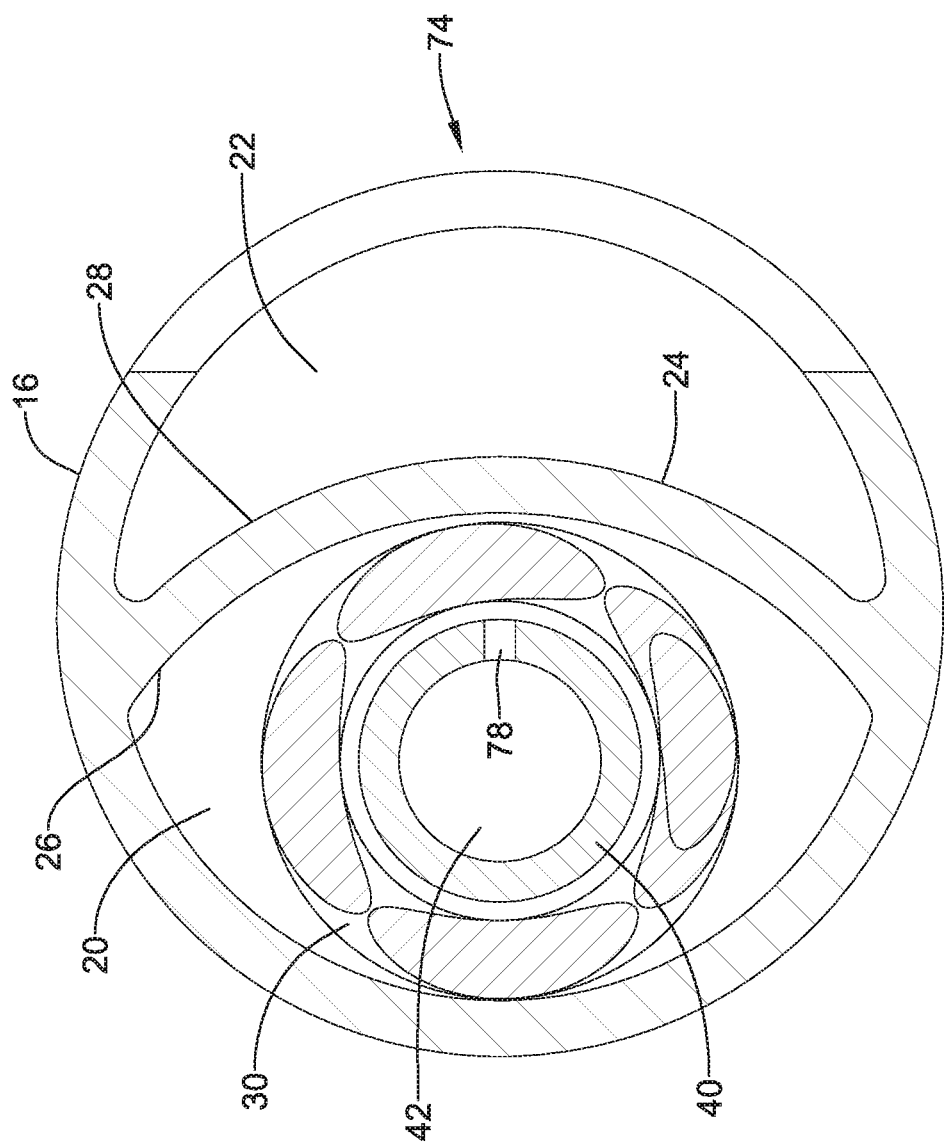
FIG. 16 is a transverse cross-sectional view of the matter elimination catheter taken along line 16-16 of FIG. 14.

Similar to the embodiment discussed above, as shown in FIG. 16, the inflow port 74 may open into the aspiration lumen 22 through a sidewall of the catheter body 16. The septum 24 may isolate the drive shaft 30, extending through the infusion lumen 20 from effluent passing into the aspiration lumen 22. Furthermore, FIG. 16 illustrates that within the distal end region, the septum 24 may have a bowed or arcuate configuration such that one of the first and second surfaces 26, 28 of the septum 24 is convex while the other of the first and second surfaces 26, 28 of the septum 24 is concave. For example, the first surface 26 of the septum 24 may be concave such that the infusion lumen 20 may have a generally elliptical or oval shape, while the second surface 28 of the septum 24 may be convex such that the aspiration lumen 22 may have a generally crescent shape. In other embodiments, the curvature of the septum 24 may be reversed, in which case the shapes of the infusion lumen 20 and the aspiration lumen 22 may also be reversed. In yet other embodiments, the septum 24 may be planar, with opposing flat surfaces.

The pressurized infusion fluid through the infusion lumen 20 interposed between the drive shaft 30 and the catheter body 16 may form a shaft fluid bearing between the drive shaft 30 and the catheter body 16 (i.e., between the outer surface of the drive shaft 30 and the inner surface of the infusion lumen 20). The shaft fluid bearing may extend from the catheter proximal portion near the manifold 12 to the catheter distal portion near the distal end of the drive shaft 30. For example, the shaft fluid bearing may extend along the length of the drive shaft 30.

The pressurized infusion fluid through the infusion lumen 20 interposed between the guide wire liner 40 or a guide wire in the guide wire lumen 42 and the drive shaft 30 may form a guide wire fluid bearing between the outer surface of the guide wire liner 40 or a guide wire and the inner surface of the drive shaft 30. The guide wire fluid bearing may extend from the catheter proximal portion near the manifold 12 to the catheter distal portion near the distal end of the drive shaft 30. For example, the guide wire fluid bearing may extend along the length of the drive shaft 30.

The infusion fluid may exit the distal end region of the catheter 10 at one or more outflow ports. For example, as shown with the arrows in FIG. 17, infusion fluid may pass through a clearance gap between the outer surface of the guide wire liner 40 and the inner surface of the bore through the cutting member 60 and out the distal opening 44. Additionally or alternatively, infusion fluid may pass between the retaining ring 66 and the catheter body 16, between the retaining ring 66 and the saddle 64, between the saddle 64 and the drive shaft 30 and/or between the cutting member 60 (e.g., the neck 62) and the saddle 64, and exit through a clearance gap between the cutting member 60 and the saddle 64. In some instances infusion fluid may also exit through gaps in the proximal, expandable cutter 60b. The pressurized infusion fluid may form a fluid bearing between one or more of these structures, such as between one or more of the guide wire liner 40, guide wire, cutting member 60, saddle 64, retaining ring 66, drive shaft 30, and catheter body 16. For example, pressurized fluid through the infusion lumen 20 interposed between the cutting member 60 and the catheter body 16 (e.g., saddle 64) may form a cutter fluid bearing between the cutting member 60 (e.g., neck 62) and the catheter body 16 (e.g., saddle 64), and/or pressurized fluid through the infusion lumen 20 interposed between the cutting member 60 and the guide wire liner 40 or guide wire may form a cutter fluid bearing between the cutting member 60 and the guide wire liner 40 or guide wire extending through the bore of the cutting member 60.

Figure 17:
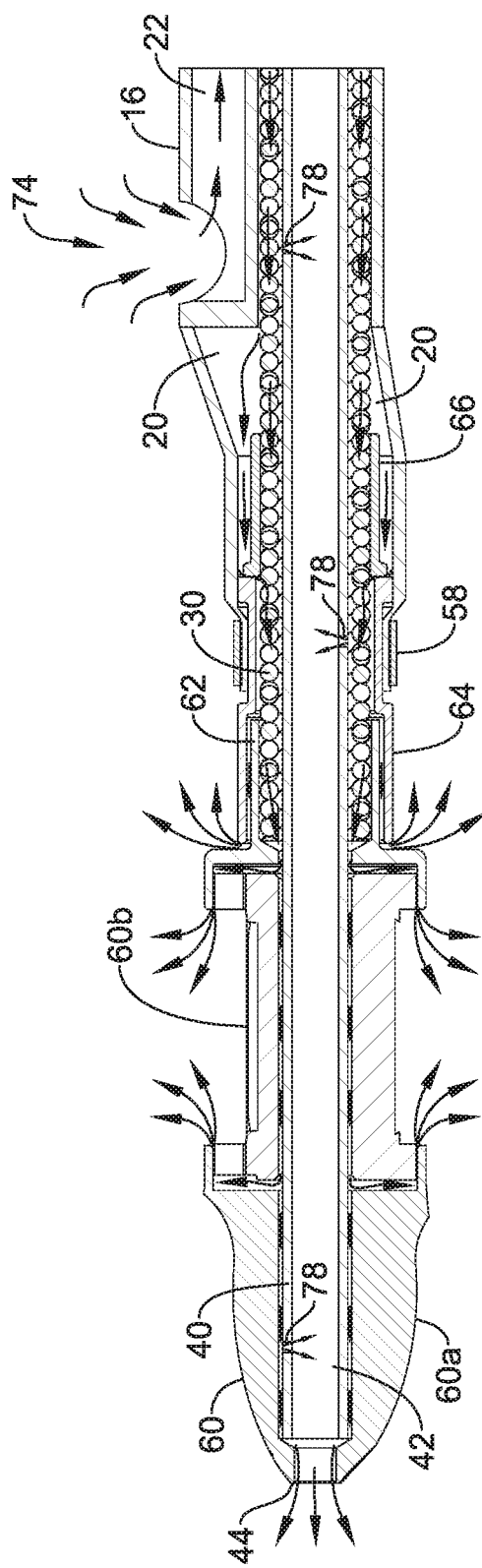
FIG. 17 is a cross-sectional view illustrating exemplary flows through the distal end region of the exemplary matter elimination catheter of FIG. 15.

In some instances, such as shown in FIGS. 15-17, the guide wire liner 40 may include one or more, or a plurality of orifices 78 extending through the sidewall of the guidewire liner 40. Although three orifices 78 are shown, in other embodiments the guide wire liner 40 may include one, two, four, five, or more orifices arranged at any desired location along the guide wire liner 40. The orifice(s) may be provided so high pressure fluid (e.g., saline, lubricant, and/or medicament) within the infusion lumen 20 passes (e.g., weeps, oozes, drips, sprays, bleeds, etc.) through the orifice 78 to continually fill the lumen of the guide wire liner 40 with saline and/or lubricant, such as Rotoglide. Arrows shown in FIG. 17 illustrate infusion fluid passing through the orifices 78 into the guide wire lumen 42 defined by the guide wire liner 40. Infusion fluid passing into the lumen of the guide wire liner 40 may help lubricate the guide wire extending therethrough, for example. One or more of the orifices 78 may optionally be located near a distal portion of the catheter 10 (e.g., distal to the drive shaft 30 and/or within the bore of the cutting member 60).

Furthermore, the pressurized infusion fluid may provide a fluid barrier to prevent ingress of effluent, including particulates such as fibrin, from entering the distal end region of the catheter 10 through the distal opening 44, between the outer surface of the guide wire liner 40 and the inner surface of the bore through the cutting member 60, between the cutting member 60 (e.g., the neck 62) and the saddle 64, between blades or other structure of the proximal, expandable cutter 60b, or other clearance gap between one or more of the guide wire liner 40, guide wire, cutting member 60, saddle 64, retaining ring 66, drive shaft 30, and catheter body 16. In other words, the pressure gradient between the pressurized infusion fluid within the distal end region of the catheter 10 and the pressure within the body lumen may permit infusion fluid to exit through one or more of these pathways, while preventing effluent to enter the distal end region of the catheter 10 through one or more of these pathways.

Also shown in FIG. 17, a vacuum may be drawn through the aspiration lumen 22 via an aspiration source (e.g., pump) in communication with the aspiration lumen 22 to draw effluent (e.g., infusion fluid and entrained particulates) into the aspiration lumen 22 through the aspiration or inflow port 74. The effluent is isolated from the drive shaft 30 via the septum 24. Therefore, the drive shaft 30 may be continuously covered with the infusion fluid, while not being fouled with particulates from the effluent.

EXAMPLES

Example 1 can include subject matter, such as can include a matter elimination catheter comprising: a catheter body extending from a catheter proximal portion to a catheter distal portion, the catheter body including: an infusion lumen an aspiration lumen fluidly isolated from the infusion lumen, and a septum of the catheter body interposed between the infusion and aspiration lumens; a drive shaft within the infusion lumen, the drive shaft configured to provide rotation near the catheter distal portion; a guide wire lumen within the drive shaft; and wherein the infusion lumen, the drive shaft and the guide wire lumen are fluidly separated from the aspiration lumen with the septum.

Example 2 can include, or can optionally be combined with the subject matter of Example 1, to optionally include wherein the septum spans the catheter body from a first portion of a catheter body side wall to a second portion of the catheter body side wall.

Example 3 can include, or can optionally be combined with the subject matter of one or any combination of Examples 1 or 2 to optionally include wherein the catheter body includes: at least one outflow port near the catheter distal portion in communication with the infusion lumen near the catheter distal portion, and at least one inflow port near the catheter distal portion in communication with the aspiration lumen near the catheter distal portion.

Example 4 can include, or can optionally be combined with the subject matter of one or any combination of Examples 1 through 3 to optionally include an infusion fluid source in communication with the infusion lumen and configured to provide a source of pressurized infusion fluid through the infusion lumen and the outflow port; an aspiration source in communication with the aspiration lumen and configured to aspirate the infusion fluid and entrained matter through the inflow port at or near the catheter distal portion and the aspiration lumen; and wherein in an operational mode the infusion fluid entrains matter from a vessel between the outflow port and the inflow port, and the entrained matter and infusion fluid are delivered to the catheter proximal portion through the aspiration lumen.

Example 5 can include, or can optionally be combined with the subject matter of one or any combination of Examples 1-4 optionally to include wherein in a pressurized configuration pressure of the infusion fluid within the infusion lumen is greater than pressure of the infusion fluid with entrained matter, and the infusion fluid with entrained matter is directed away from the drive shaft within the infusion lumen according to the pressure difference.

Example 6 can include, or can optionally be combined with the subject matter of Examples 1-5 to optionally include a guide wire liner within the guide wire lumen of the drive shaft, wherein the drive shaft is rotatable relative to the guide wire liner.

Example 7 can include, or can optionally be combined with the subject matter of Examples 1-6 to optionally include one or more fluid bearings isolated from the aspiration lumen and generated with pressurized infusion fluid delivered through the infusion lumen.

Example 8 can include, or can optionally be combined with the subject matter of Examples 1-7 to optionally include wherein the one or more fluid bearings include one or more of fluid dynamic bearings or hydrostatic bearings.

Example 9 can include, or can optionally be combined with the subject matter of Examples 1-8 to optionally include at least one shaft fluid bearing interposed between the catheter body and the drive shaft in the infusion lumen, and the at least one shaft fluid bearing is generated with pressurized infusion fluid delivered through the infusion lumen.

Example 10 can include, or can optionally be combined with the subject matter of Examples 1-9 to optionally include wherein the at least one shaft fluid bearing extends from the catheter proximal portion to the catheter distal portion.

Example 11 can include, or can optionally be combined with the subject matter of Examples 1-10 to optionally include wherein the at least one shaft fluid bearing extends the length of the drive shaft.

Example 12 can include, or can optionally be combined with the subject matter of Examples 1-11 to optionally include at least one guide wire fluid bearing interposed between the drive shaft and at least one of a guide wire or a guide wire liner in the guide wire lumen, wherein the at least one guide wire fluid bearing is generated with pressurized infusion fluid delivered through the infusion lumen and penetrating the drive shaft.

Example 13 can include, or can optionally be combined with the subject matter of Examples 1-12 to optionally include wherein the drive shaft is coupled to at least one rotatable cutter near the catheter distal portion, and the drive shaft and the at least one rotatable cutter are rotatable in a clockwise and/or a counter clock-wise direction relative to the catheter body.

Example 14 can include, or can optionally be combined with the subject matter of Examples 1-13 to optionally include wherein at least one cutter fluid bearing is interposed between the rotatable cutter and the catheter body, and the at least one cutter fluid bearing is formed between a cutter interface and a catheter body interface with pressurized infusion fluid delivered from the infusion lumen.

Example 15 can include, or can optionally be combined with the subject matter of Examples 1-14 to optionally include a catheter body extending from a catheter proximal portion to a catheter distal portion, the catheter body including: an infusion lumen in fluid communication with at least one outflow port near the catheter distal portion, an aspiration lumen isolated from the infusion lumen, and a septum of the catheter body interposed between the infusion and aspiration lumens; a drive shaft within the infusion lumen, the drive shaft configured to provide rotation near the catheter distal portion; and wherein in an infusion configuration an infusion fluid is delivered through the infusion lumen to the at least one outflow port: the drive shaft and a portion of the catheter body associated with the infusion lumen are configured to provide at least one shaft fluid bearing therebetween with the infusion fluid, and wherein the at least one outflow port is configured to provide a fluid barrier with the infusion fluid to prevent ingress of infusion fluid with entrained matter into the infusion lumen.

Example 16 can include, or can optionally be combined with the subject matter of Examples 1-15 to optionally include wherein the infusion lumen, the drive shaft and a guide wire lumen within the drive shaft are separated from the aspiration lumen with the septum.

Example 17 can include, or can optionally be combined with the subject matter of Examples 1-16 to optionally include wherein the septum spans the catheter body from a first portion of a catheter body side wall to a second portion of the catheter body side wall.

Example 18 can include, or can optionally be combined with the subject matter of Examples 1-17 to optionally include wherein the fluid barrier prevents ingress of the infusion fluid with entrained matter according to a first pressure of the infusion fluid within the infusion lumen being greater than a second pressure of the infusion fluid with the entrained matter.

Example 19 can include, or can optionally be combined with the subject matter of Examples 1-18 to optionally include wherein in the infusion configuration an interior surface of the drive shaft and at least one of a guide wire or a guide wire liner within a guide wire lumen of the drive shaft are configured to provide at least one guide wire fluid bearing with the infusion fluid.

Example 20 can include, or can optionally be combined with the subject matter of Examples 1-19 to optionally include wherein the infusion fluid penetrates the drive shaft to provide the at least one guide wire fluid bearing.

Example 21 can include, or can optionally be combined with the subject matter of Examples 1-20 to optionally include wherein the at least one shaft fluid bearing is isolated from the aspiration lumen by the fluid barrier and the septum.

Example 22 can include, or can optionally be combined with the subject matter of Examples 1-20 to optionally include wherein the at least one shaft fluid bearing extends from the catheter proximal portion to the catheter distal portion.

Example 23 can include, or can optionally be combined with the subject matter of Examples 1-22 to optionally include wherein the at least one shaft fluid bearing extends substantially the length of the drive shaft.

Example 24 can include, or can optionally be combined with the subject matter of Examples 1-23 to optionally include wherein the drive shaft is coupled to at least one rotatable cutter near the catheter distal portion, and the drive shaft and the at least one rotatable cutter are rotatable in a clockwise and/or counter clockwise direction relative to the catheter body.

Example 25 can include, or can optionally be combined with the subject matter of Examples 1-24 to optionally include wherein in the infusion configuration the at least one rotatable cutter and the catheter body are configured to provide at least one cutter fluid bearing therebetween with the infusion fluid.

Example 26 can include, or can optionally be combined with the subject matter of Examples 1-25 to optionally include a manifold coupled to the catheter proximal portion, the manifold comprising an infusion port configured to deliver infusion fluid to the infusion lumen.

Example 27 can include, or can optionally be combined with the subject matter of Examples 1-26 to optionally include wherein the manifold further comprises: a composite lumen, the composite lumen receiving a proximal portion of the drive shaft, and a seal, wherein the drive shaft and a guide wire lumen within the drive shaft extend through the seal.

Example 28 can include, or can optionally be combined with the subject matter of Examples 1-27 to optionally include wherein the manifold further comprises a diversion sleeve positioned around the drive shaft and extending proximally relative to the infusion port.

Example 29 can include, or can optionally be combined with the subject matter of Examples 1-28 to optionally include wherein in the infusion configuration the infusion fluid is directed distally over an exterior perimeter of the diversion sleeve, and at a distal end of the diversion sleeve a first portion of the infusion fluid flows distally through the infusion lumen toward the catheter distal portion and a second portion of the infusion fluid flows proximally along an interior perimeter of the diversion sleeve, the first and second portions controlled by the dimensions between the interior perimeter of the diversion sleeve and the drive shaft.

Example 30 can include, or can optionally be combined with the subject matter of Examples 1-29 to optionally include wherein the diversion sleeve and the drive shaft are configured to provide a second shaft fluid bearing therebetween with the second portion of the infusion fluid.

Example 31 can include, or can optionally be combined with the subject matter of Examples 1-30 to optionally include wherein the drive shaft and at least one of a guide wire or guide wire lumen are configured to provide a guide wire fluid bearing with the first portion of the infusion fluid.

Example 32 can include a method of using of a matter elimination catheter in accordance with the subject matter of Examples 1-31, including one or more of the following steps: A) aspirating in the aspiration lumen, B) infusing infusion fluid in the infusion lumen, the infusion lumen including a drive shaft and a guide wire lumen separated from the aspiration lumen, C) lubricating the drive shaft in the infusion lumen and/or lubricate the guide wire in the infusion lumen/guide wire lumen, D) preventing ingress of infusion fluid with entrained matter into the infusion lumen with a fluid barrier, and E) optionally forming a fluid bearing for one or more of the drive shaft in the infusion lumen with infusion fluid or for a guide wire configured for positioning within the drive shaft.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A matter elimination catheter, comprising:
a catheter body extending from a catheter proximal portion to a catheter distal portion, the catheter body including an infusion lumen;
a drive shaft disposed within the infusion lumen, the drive shaft being configured to provide rotation to at least one rotatable cutter coupled to the drive shaft near the catheter distal portion; and
a guide wire liner extending through the drive shaft, the guide wire liner defining a guide wire lumen therein, wherein the drive shaft is rotatable relative to the guide wire liner;
wherein pressurized infusion fluid delivered through the infusion lumen and flowing distally between an outer surface of the guide wire liner and an inner surface of the infusion lumen forms a first guide wire fluid bearing interposed between an outer surface of the guide wire liner and an inner surface of the at least one rotatable cutter, wherein the first guide wire fluid bearing is generated with pressurized infusion fluid delivered through the infusion lumen and flowing distally between the outer surface of the guide wire liner and an inner surface of at least one rotatable cutter.

2. The matter elimination catheter of claim 1, further comprising a pressurized infusion fluid source in fluid communication with the infusion lumen and configured to provide pressurized infusion fluid delivered to at least one outflow port and delivered through at least one orifice extending through a sidewall of the guide wire liner to form the first guide wire fluid bearing.

3. The matter elimination catheter of claim 2, wherein the catheter body further comprises an aspiration lumen fluidly isolated from the infusion lumen.

4. The matter elimination catheter of claim 3, wherein the aspiration lumen terminates with least one inflow port near the catheter distal portion.

5. The matter elimination catheter of claim 4, wherein the infusion lumen terminates at a point distal of a distalmost at least one inflow port.

6. The matter elimination catheter of claim 3, further comprising an aspiration source in communication with the aspiration lumen and configured to draw effluent including infusion fluid and entrained particulates into and through the infusion lumen.

7. The matter elimination catheter of claim 6, wherein the pressurized infusion fluid source and the aspiration source are configured to maintain an isovolumetric treatment site.

8. The matter elimination catheter of claim 6, wherein the pressurized infusion fluid source and the aspiration source are configured to maintain a pressure differential between the pressurized infusion fluid within the infusion lumen and aspirated infusion fluid and entrained particulates within the infusion lumen.

9. The matter elimination catheter of claim 6, wherein the pressurized infusion fluid source is configured to deliver infusion fluid through the at least one outflow port sufficient to provide a fluid barrier at the at least one outflow port that prevents ingress of particulates.

10. A matter elimination catheter, comprising:
a catheter body extending from a catheter proximal portion to a catheter distal portion, the catheter body including an infusion lumen and an aspiration lumen; and
a drive shaft disposed within the infusion lumen, the drive shaft being configured to provide rotation to at least one rotatable cutter coupled to the drive shaft near the catheter distal portion; and
a guide wire liner extending through the drive shaft, the guide wire liner defining a guide wire lumen therein, wherein the drive shaft is rotatable relative to the guide wire liner;
wherein pressurized infusion fluid delivered through the infusion lumen and flowing distally between an outer surface of the guide wire liner and an inner surface of the infusion lumen forms a first guide wire fluid bearing interposed between an outer surface of the guide wire liner and an inner surface of the at least one rotatable cutter, wherein the first guide wire fluid bearing is generated with pressurized infusion fluid delivered through the infusion lumen and flowing distally between the outer surface of the guide wire liner and the inner surface of the at least one rotatable cutter,
wherein the infusion lumen is in fluid communication with a pressurized infusion fluid source,
wherein the aspiration lumen is in fluid communication with an aspiration source configured to draw effluent including infusion fluid and entrained particulates into and through the aspiration lumen.

11. The matter elimination catheter of claim 10, wherein the pressurized infusion fluid source and the aspiration source are configured to maintain an isovolumetric treatment site.

12. The matter elimination catheter of claim 10, wherein the aspiration lumen terminates with at least one inflow port near the catheter distal portion.

13. The matter elimination catheter of claim 12, wherein the infusion lumen terminates at a point distal of a distalmost at least one inflow port.

14. The matter elimination catheter of claim 10, wherein the pressurized infusion fluid source is configured to deliver infusion fluid through at least one outflow port sufficient to provide a fluid barrier at the at least one outflow port that prevents ingress of particulates.

15. A method of using of a matter elimination catheter having catheter body comprising:
an infusion lumen in fluid communication with a pressurized infusion fluid source;
an aspiration lumen in fluid communication with an aspiration source configured to draw effluent including infusion fluid and entrained particulates into and through the aspiration lumen,
wherein the infusion lumen and the aspiration lumen are separated by a fluid barrier;
a drive shaft disposed within the infusion lumen, the drive shaft being configured to provide rotation to at least one rotatable cutter; and
a guide wire liner defining a guide wire lumen,
wherein pressurized infusion fluid delivered to at least one outflow port and through at least one orifice extending through a side wall of the guide wire liner and flowing distally between an outer surface of the guide wire liner and an inner surface of the infusion lumen forms a first guide wire fluid bearing between the guide wire liner and the at least one rotatable cutter, the method comprising:
rotating the drive shaft and the at least one rotatable cutter;
infusing pressurized infusion fluid through the infusion lumen,
through at least one orifice extending through a side wall of the guide wire liner,
between the guide wire liner and the at least one rotatable cutter, and
through at least one outflow port,
lubricating the drive shaft within the infusion lumen;
lubricating the rotatable cutter about the guide wire liner;
preventing ingress of infusion fluid with entrained matter into the infusion lumen with a fluid barrier; and
aspirating in the aspiration lumen.

16. The method of claim 15, wherein the pressurized infusion fluid source and the aspiration source are configured to maintain a pressure differential between the pressurized infusion fluid within the infusion lumen and aspirated infusion fluid and entrained particulates within the infusion lumen.

17. The method of claim 15, wherein the infusion lumen terminates at a point distal of a distalmost at least one inflow port.

18. The method of claim 15, wherein infusing pressurized infusion fluid through the infusion lumen further lubricates a guide wire positioned within the drive shaft.

19. The method of claim 15, further comprising:
maintaining an isovolumetric treatment site between the at least one outflow port and an inflow port in fluid communication with the aspiration lumen.

20. The method of claim 15, wherein the at least one rotatable cutter is rotatable relative to the guide wire liner.

* * * * *